United States Patent
Ulloa-Cerna et al.

(10) Patent No.: US 11,756,688 B2
(45) Date of Patent: Sep. 12, 2023

(54) ECG-BASED CARDIOVASCULAR DISEASE DETECTION SYSTEMS AND RELATED METHODS

(71) Applicants: Tempus Labs, Inc., Chicago, IL (US); Geisinger Clinic, Danville, PA (US)

(72) Inventors: Alvaro E. Ulloa-Cerna, Danville, PA (US); Noah Zimmerman, Chicago, IL (US); Greg Lee, Chicago, IL (US); Christopher M. Haggerty, Danville, PA (US); Brandon K. Fornwalt, Danville, PA (US); Ruijun Chen, Danville, PA (US); John Pfeifer, Danville, PA (US); Christopher Good, Danville, PA (US)

(73) Assignees: Tempus Labs, Inc., Chicago, IL (US); Geisinger Clinic, Danville, PA (US)

( * ) Notice: Subject to any disclaimer, the term of this patent is extended or adjusted under 35 U.S.C. 154(b) by 0 days.

(21) Appl. No.: 17/829,351

(22) Filed: May 31, 2022

(65) Prior Publication Data

US 2022/0384044 A1    Dec. 1, 2022

Related U.S. Application Data

(60) Provisional application No. 63/224,850, filed on Jul. 22, 2021, provisional application No. 63/202,436, (Continued)

(51) Int. Cl.
  *G16H 50/30* (2018.01)
  *G16H 50/20* (2018.01)
  (Continued)

(52) U.S. Cl.
  CPC ........ *G16H 50/30* (2018.01); *A61B 5/0006* (2013.01); *A61B 5/28* (2021.01); *A61B 5/318* (2021.01);
  (Continued)

(58) Field of Classification Search
  CPC ........ G16H 50/30; G16H 50/00–50/80; A61B 5/0006; A61B 5/28; A61B 5/30–5/308;
  (Continued)

(56) References Cited

U.S. PATENT DOCUMENTS 7,801,591 B1 * 9/2010 Shusterman ........... G16H 50/20
                                                        600/509
10,667,680 B2   6/2020 Gupta et al.
(Continued)

FOREIGN PATENT DOCUMENTS

CN     106510686 A    3/2017
KR    2020007852 A    7/2020
(Continued)

OTHER PUBLICATIONS

Arvanitis et al., Identification of V1221 (Val122Ile) Transthyretin Cardiac Amyloidosis (ATTR) Using Serum Retinol-Binding Protein 4 (RBP4) and a Clinical Prediction Model, JAMA Cardiol., 2017, 2(3):305-313.
(Continued)

*Primary Examiner* — Jonathan T Kuo
(74) *Attorney, Agent, or Firm* — Quarles & Brady LLP

(57) ABSTRACT

A method for determining cardiology disease risk from electrocardiogram trace data and clinical data includes receiving electrocardiogram trace data associated with a patient, receiving the patient's clinical data, providing both sets of data to a trained machine learning composite model that is trained to evaluate the data with respect to each disease of a set of cardiology diseases including three or more of cardiac amyloidosis, aortic stenosis, aortic regurgitation, mitral stenosis, mitral regurgitation, tricuspid regurgitation, abnormal reduced ejection fraction, or abnormal interventricular septal thickness, generating, by the model and based on the evaluation, a composite risk score reflecting a likelihood of the patient being diagnosed with one or more of the cardiology diseases within a predetermined period of time from when the electrocardiogram trace data (Continued)

was generated, and outputting the composite risk score to at least one of a memory or a display.

29 Claims, 13 Drawing Sheets

Related U.S. Application Data filed on Jun. 10, 2021, provisional application No. 63/194,923, filed on May 28, 2021.

(51) Int. Cl.
*A61B 5/318* (2021.01)
*A61B 5/00* (2006.01)
*A61B 5/28* (2021.01)
*G06F 18/214* (2023.01)

(52) U.S. Cl.
CPC ............ *A61B 5/7275* (2013.01); *G16H 50/20* (2018.01); *G06F 18/2155* (2023.01)

(58) Field of Classification Search
CPC . A61B 5/318–367; A61B 5/72–5/7296; A61B 5/74–5/7495; G06K 9/6259
See application file for complete search history.

(56) References Cited

U.S. PATENT DOCUMENTS

| | | | |
|---|---|---|---|
| 10,827,982 B2 * | 11/2020 | Sitek | G06N 3/0454 |
| 2007/0214013 A1 * | 9/2007 | Silverman | G16H 20/40 600/300 |
| 2009/0093686 A1 | 4/2009 | Hu et al. | |
| 2010/0217144 A1 | 8/2010 | Brian | |
| 2011/0295134 A1 * | 12/2011 | DeBauche | A61B 5/0006 600/509 |
| 2015/0112182 A1 | 4/2015 | Sharma et al. | |
| 2015/0235143 A1 | 8/2015 | Eder | |
| 2015/0324527 A1 | 11/2015 | Siegel et al. | |
| 2016/0022162 A1 | 1/2016 | Ong et al. | |
| 2016/0135706 A1 | 5/2016 | Sullivan et al. | |
| 2017/0357756 A1 | 12/2017 | Fidone et al. | |
| 2018/0333104 A1 * | 11/2018 | Sitek | G06N 5/046 |
| 2019/0171936 A1 | 6/2019 | Karras et al. | |
| 2020/0176122 A1 | 6/2020 | Teplitzky et al. | |
| 2020/0226757 A1 | 7/2020 | Hare, II et al. | |
| 2020/0337773 A1 | 10/2020 | Rawlinson et al. | |
| 2020/0353271 A1 | 11/2020 | Dani et al. | |
| 2020/0397313 A1 * | 12/2020 | Attia | A61B 5/318 |
| 2021/0000347 A1 | 1/2021 | Stump | |
| 2021/0027194 A1 | 1/2021 | Monaghan et al. | |
| 2021/0059540 A1 * | 3/2021 | Peterson | A61B 5/349 |
| 2021/0076960 A1 | 3/2021 | Fornwalt et al. | |
| 2021/0085215 A1 | 3/2021 | Auerbach et al. | |
| 2021/0089921 A1 | 3/2021 | Aghdasi et al. | |
| 2021/0110930 A1 | 4/2021 | Park et al. | |
| 2021/0150693 A1 | 5/2021 | Fornwalt et al. | |
| 2021/0153761 A1 * | 5/2021 | Jung | G06N 20/20 |
| 2021/0259560 A1 * | 8/2021 | Venkatraman | G16H 40/63 |
| 2021/0345934 A1 * | 11/2021 | Landgraf | A61B 7/04 |
| 2022/0229071 A1 * | 7/2022 | Rhyne | A61P 9/00 |

FOREIGN PATENT DOCUMENTS

| | | | |
|---|---|---|---|
| WO | 2020004369 A1 | 1/2020 | |
| WO | 2021071142 A1 | 4/2021 | |

OTHER PUBLICATIONS

Ashburner et al., Design and Rationale of a Pragmatic Trial Integrating Routine Screening for Atrial Fibrillation at Primary Care Visits: The VITAL-AF Trial, American Heart Journal, 2019, 215:147-156.
Attia et al., An Artificial Intelligence-Enabled ECG Algorithm for the Identification of Patients with Atrial Fibrillation During Sinus Rhythm: A Retrospective Analysis of Outcome Prediction, The Lancet, 2019, 394(10201):861-867.
Freedman et al., Stroke Prevention in Atrial Fibrillation, The Lancet, 2016, 388(10046):806-817.
Gladstone et al.,, Screening for Atrial Fibrillation in the Older Population: A Randomized Clinical Trial, JAMA Cardiology, 2021, 6(5):558-567.
Hindricks et al., 2020 ESC Guidelines for the Diagnosis and Management of Atrial Fibrillation Developed in Collaboration with the European Association for Cardio-Thoracic Surgery (EACTS), European Heart Journal, 2020, 42(5):373-498.
Huda et al., A Machine Learning Model for Identifying Patients at Risk for Wild-Type Transthyretin Amyloid Cardiomyopathy, Nature Communications, 2021, 12:2725, pp. 1-12.
Khurshid et al., ECG-Based Deep Learning and Clinical Risk Factors to Predict Atrial Fibrillation, Circulation, 2022, 145(2):122-133.
Kyriakou et al., Diagnosis of Cardiac Amyloidosis: A Systematic Review on the Role of Imaging and Biomarkers, BMC Cardiovascular Disorders, 2018, 18:221, pp. 1-11.
Lip et al., Refining Clinical Risk Stratification for Predicting Stroke and Thromboembolism in Atrial Fibrillation Using a Novel Risk Factor-Based Approach: The Euro Heart Survey on Atrial Fibrillation, Chest, 2010, 137(2):263-272.
Martini et al., Deep Learning to Diagnose Cardiac Amyloidosis from Cardiovascular Magnetic Resonance, Journal of Cardiovascular Magnetic Resonance, 2020, 22:84, pp. 1-11.
Poterucha et al., Deep Learning Analysis of Cardiac Testing for the Detection of Cardiac Amyloidosis, JACC, 2021, 77(18):529.
Raghunath et al., Prediction of Mortality from 12-lead Electro Cardiogram Voltage Data Using a Deep Neural Network, Nature Medicine, 2020, 26(6):886-891.
Raghunath et al., Deep Neural Networks can Predict New-Onset Atrial Fibrillation from the 12-lead ECG and Help Identify Those at Risk of Atrial Fibrillation-Related Stroke, Circulation, 2021, 143(13):1287-1298.
Singer et al., ReducinG stroke by screening for UndiAgnosed atRial fibrillation in elderly inDividuals (GUARD-AF): Rationale and Design of the GUARD-AF Randomized Trial of Screening for Atrial Fibrillation with a 14-day Patch-Based Continuous ECG Monitor, American Heart Journal, 2022, 249:76-85.
Steinhubl et al., Effect of a Home-Based Wearable Continuous ECG Monitoring Patch on Detection of Undiagnosed Atrial Fibrillation: The mSToPS Randomized Clinical Trial, JAMA, 2018, 320(2):146-155.
Suresh et al., Advanced Cardiac Amyloidosis Associated with Normal Interventricular Septum Thickness: An Uncommon Presentation of Infiltrative Cardiomyopathy, J Am Soc Echocardiogr, 2014, 27(4):440-447.
Svennberg et al., Mass Screening for Untreated Atrial Fibrillation: The STROKESTOP Study, Circulation, 2015, 131(25):2176-2184.
Topol, Digital Medicine—What's Lurking in Your Electrocardiogram?, The Lancet, 2021, 397:785.
US Preventive Services Task Force, Screening for Atrial Fibrillation, US Preventive Services Task Force Recommendation Statement, JAMA, 2022, 327(4):360-367.
Weimann et al., Transfer Learning for ECG Classification, Scientific Reports, 2021, 11:5251, pp. 1-12.
Wolf et al., Atrial Fibrillation as an Independent Risk Factor for Stroke: The Framingham Study, Stroke, 1991, 22(8):983-988.
PCT International Search Report and Written Opinion, PCT/US2022/031663, dated Aug. 19, 2022, 15 pages.
PCT International Search Report and Written Opinion, PCT/US2022/031665, dated Aug. 19, 2022, 16 pages.
PCT International Search Report and Written Opinion, PCT/US2022/031670, dated Aug. 18, 2022, 9 pages.
Apple Inc., De Novo Classification Request for ECG App, 2018, 15 pages.

* cited by examiner

ECG-BASED CARDIOVASCULAR DISEASE DETECTION SYSTEMS AND RELATED METHODS

CROSS-REFERENCE TO RELATED APPLICATIONS

This application claims the benefit of U.S. provisional application 63/194,923, filed May 28, 2021, U.S. provisional application 63/202,436, filed Jun. 10, 2021, and U.S. provisional application 63/224,850, filed Jul. 22, 2021.

BACKGROUND

Echocardiography is an important diagnostic test for many heart diseases, including valvular disease, left ventricular (LV) dysfunction, and various cardiomyopathies. These diseases carry a high burden of morbidity and mortality, and findings from transthoracic echocardiography (TTE) hold important evidence-based implications for diagnosis and prognosis.

Currently, echocardiography is not generally used as a screening tool given the low prevalence of disease in the general population. Therefore, indicated use of TTE is instead typically triggered by some kind of symptom, adverse event, or physical exam or incidental finding leading to suspicion of heart disease, thereby raising the pretest probability and likelihood of finding a clinically impactful or actionable disease. However, a significant gap remains in that a large number of patients, in meeting that triggered indication for suspected disease, will have already suffered an adverse event, a symptom affecting their quality of life, or an irreversible pathophysiologic change from their undiagnosed disease.

For example, in severe aortic stenosis (AS), the initial presenting symptom is syncope for 10-11% of patients, reduced EF for 8%, and angina for 35-41% of patients, which may lead to falls, hip fractures, or irreversibly reduced functional status.

Early diagnosis of valvular disease or cardiomyopathy has been shown to improve outcomes, yet despite the wide range of indications and increasing availability of TTE, these conditions continue to be underdiagnosed or diagnosed too late, suggesting that broader methods of detection are required.

SUMMARY OF THE INVENTION

In one aspect, a method for determining cardiology disease risk from electrocardiogram trace data and clinical data, includes the steps of: receiving electrocardiogram trace data associated with a patient; receiving clinical data associated with the patient; providing the electrocardiogram trace data and clinical data to a trained machine learning composite model, the model trained to evaluate the electrocardiogram trace data and the clinical data with respect to each disease of a set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness; generating, by the trained machine learning composite model and based on the evaluation, a composite risk score reflecting a likelihood of the patient being diagnosed with one or more of the cardiology diseases of the set of cardiology diseases within a predetermined period of time from when the electrocardiogram trace data was generated; and outputting the composite risk score to at least one of a memory or a display.

In another aspect, a system for determining cardiology disease risk from electrocardiogram trace data and clinical data includes a computer including a processing device. The processing device is configured to: receive electrocardiogram trace data associated with a patient; receive clinical data of the patient; provide the electrocardiogram trace data and clinical data to a trained composite model, the trained composite model being trained to generate a risk score based on the electrocardiogram trace data and the clinical data; wherein the risk score reflects a likelihood of a patient having one or more of all of a set of cardiology diseases, the set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness; receive a risk score indicative of a likelihood the patient will suffer from one of the diseases in the set of cardiology diseases within a predetermined period of time from when the electrocardiogram trace data was generated; and output the risk score to at least one of a memory or a display.

In yet another aspect, a non-transitory computer readable medium, comprising instructions for causing a computer to: receive electrocardiogram trace data associated with a patient; receive clinical data of the patient; provide the electrocardiogram trace data and clinical data to a trained composite model, the trained composite model being trained to generate a risk score based on the electrocardiogram trace data and the clinical data; wherein the risk score reflects a likelihood of a patient having one or more of all of a set of cardiology diseases, the set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness; receive a risk score indicative of a likelihood the patient will suffer from one of the diseases in the set of cardiology diseases within a predetermined period of time from when the electrocardiogram trace data was generated; and output the risk score to at least one of a memory or a display.

DETAILED DESCRIPTION

Figure 1:
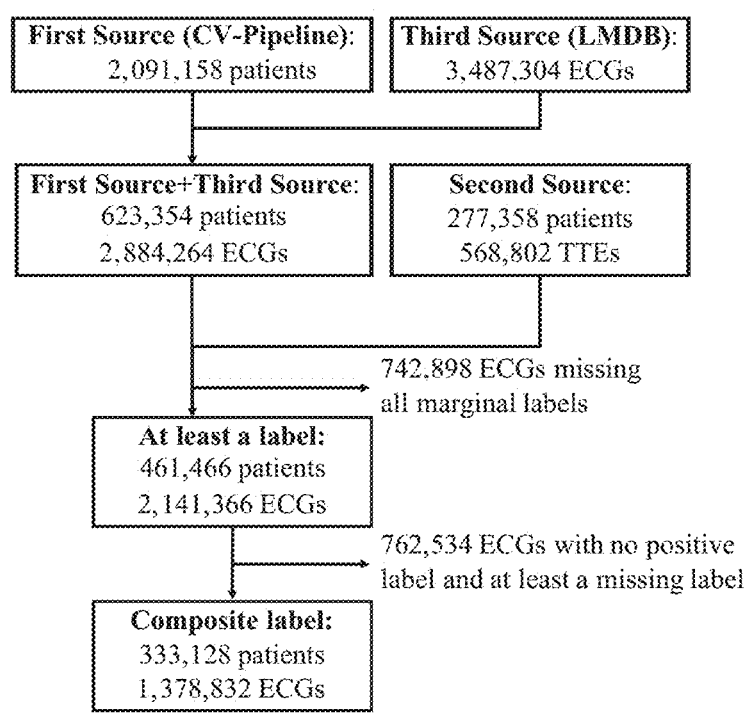
FIG. 1 is a block diagram of source data to dataset used for experiments described in this disclosure.

A system and method for generating and applying a composite model is disclosed herein. In some embodiments, the composite model is an ECG-based machine-learning composite model. In some embodiments, the composite model can predict a composite heart disease endpoint. In some embodiments, a composite model yields a higher positive outcome metric, such as a positive predictive value (PPV), to facilitate more practical recommendation of echocardiography to improve under-diagnosis of heart disease. In some embodiments, the composite model comprises an electrocardiogram (ECG)-based machine learning approach to predict multiple heart disease endpoints simultaneously.

A composite model may be used, for example, to identify high-risk patients. The composite model may use data more ubiquitously available than TTEs, such as 12-lead electrocardiograms (ECGs). ECGs are far more common, inexpensive, and performed for a much broader range of indications, including on asymptomatic patients (for example in the preoperative setting). The composite model may thus serve as a screening tool such that patients identified as high risk could be referred for diagnostic TTE.

In some embodiments, the composite model may be used to identify patients at high risk for any one of numerous heart disease endpoints within a single ECG platform, including moderate or severe valvular disease (aortic stenosis [AS], aortic regurgitation [AR], mitral stenosis [MS], mitral regurgitation [MR], tricuspid regurgitation [TR], reduced left ventricular ejection fraction [EF], and increased interventricular septal [IVS] thickness). The composite model may generate a composite prediction with higher yield/PPV that would facilitate a more practical clinical recommendation for follow-up diagnostic echocardiography.

Clinically, a composite model can enable targeted TTE screening to help detect unrecognized and underdiagnosed diseases. A composite model may have both high sensitivity and precision. The composite model can help guide the decision to obtain a TTE even for asymptomatic patients, shifting the balance to a scenario where TTE can be effective as a screening tool downstream of an ECG, and helping clinicians diagnose patients at the right time to prevent downstream adverse events, optimize the timing of interventions, and better implement evidence-based monitoring or management.

A machine-learning composite model using only ECG-based inputs can predict multiple important cardiac endpoints within a single platform with both good performance and high PPV, thereby representing a practical tool with which to better target TTE to detect undiagnosed disease. As shown in Example 1, below, an exemplary composite model is described and confirmatory results through retrospective real-world deployment scenarios are provided, to show the large impact that such a model can have on patients when deployed across a health system. These approaches to both clinical predictions and simulated deployment represent practical solutions for existing limitations in the implementation of machine learning in healthcare.

In some embodiments, the machine learning composite model may be trained to predict composite echocardiography-confirmed disease within a certain period of time. For example, the composite model may be trained to predict composite disease within 1 year. In some embodiments, the machine learning composite model may be trained to predict 2, 3, 4, 5, 6, 7, or more diseases. For example, an exemplary composite model may be trained to predict moderate or severe valvular disease. As another example, a composite model may be trained to predict one or more of aortic stenosis, aortic regurgitation, mitral stenosis, mitral regurgitation, tricuspid regurgitation, abnormally reduced ejection fraction, and abnormal interventricular septal thickness.

A composite model may be employed as part of a system described, for instance, in U.S. Patent Publication No. 2021/0076960, titled ECG Based Future Atrial Fibrillation Predictor Systems and Methods, the contents of which are incorporated herein by reference in their entirety for all purposes.

Example 1

In one example, an ECG-based cardiovascular disease detection system may employ a machine-learning platform comprising a composite model which can effectively predict clinically significant valvular disease, reduced left ventricular EF, and increased septal thickness with excellent performance (AUROC 91.4%) by using only ECG traces, age, and sex. Furthermore, the combination of these distinct endpoints into a single platform tied to a recommendation for a singular, practical clinical response—follow-up echocardiography—resulted in an overall PPV of 52.2% for a clinically meaningful disease while maintaining high sensitivity (90%) and specificity (75.5%). This novel approach of combining multiple endpoints which align in the same recommended clinical action enables the model to leverage the increased prevalence and probability of any one disease state occurring to improve predictive performance for potential clinical implementation.

Moreover, this approach may have potential clinical utility in a retrospective deployment scenario. In one example, a retrospective deployment scenario was trained on data pre-existing relative to a first point in time (e.g., data prior to 2010) and deployed on all patients without prior disease who obtained an ECG after that first point in time (e.g., from 2010 until some data endpoint), maintaining similarly high performance as compared to the main cross-validation results based only on passive observation and standard clinical care. With an active deployment of the present platform, even higher yields/PPV may be achieved once clinicians can pursue active intervention in the form of follow-up TTE or more detailed history-taking and physical examination based on the model.

Using 2,141,366 ECGs linked to structured echocardiography and electronic health record data from 461,466 adults, a machine learning composite model was trained to predict composite echocardiography-confirmed disease within 1 year. Seven exemplary diseases were included in the composite label: moderate or severe valvular disease (aortic stenosis or regurgitation, mitral stenosis (MS) or regurgitation, tricuspid regurgitation), reduced ejection fraction (EF)<50%, or interventricular septal thickness >15 mm. In other examples, the model may be trained to predict other echocardiography-confirmed diseases, including infiltrative diseases, hypertrophic cardiomyopathy, or concentric remodeling. Such other diseases may be predicted by modifying the model to include different input data and/or input data unique to the disease being predicted. Alternatively, the input data used to train the data to identify one or more of the exemplary diseases discussed above also may be relevant to one or more of these additional diseases, such that new or additional data may not be needed to train the model to predict the additional disease(s). In still other examples, other clinical thresholds besides 50% for abnormal reduced ejection fraction or 15 mm for abnormal interventricular septal thickness may be used. Composite model performance was evaluated using both 5-fold cross-validation and a simulated retrospective deployment scenario. Various combinations of input variables (demographics, labs, structured ECG data, ECG traces) were also tested. The composite model with age, sex and ECG traces had an AUROC of 91.4% and a PPV of 52.2% at 90% sensitivity. Individual disease model PPVs were lower, ranging from 2.1% for MS to 41.3% for reduced EF. A simulated retrospective deployment model had an AUC of 88.8% on data trained pre-2010 and, when deployed on at-risk patients in 2010, identified 22% of patients as high-risk with a PPV of 40%. The AUROC for different variable inputs ranged from 84.7% to 93.2%.

Data was retrieved and processed from three clinical sources from a first entity, including 2,091,158 patients from a first source comprising an electronic health record (EHR), 568,802 TTEs from a second source, and 3,487,304 ECG traces from a third source. In another embodiment, it will be understood that data may be obtained from a plurality of sources related to a plurality of different or unrelated entities. From this data all ECGs after a first point in time (e.g., 1984) from patients 18 years old, sampled at either 250 hz or 500 hz with at least 8 leads, and with a corresponding medical record from the first source were included. This intersection of the first and third sources yielded 2,884,264 ECGs from 623,354 patients.

Vitals, labs, and demographics as of the ECG acquisition time were also obtained. Table 1 lists inputs grouped by category, although it will be appreciated that the model may utilize one or more other inputs within the categories listed or within one or more other categories. Each input is shown with its units in parenthesis. The ECG findings were binary.

The closest past measurement to the ECG was used unless the measurement was older than a year, in which case a missing value was assigned. TTE measurements and diagnoses (AS, AR, MR, MS, and TR) were extracted from reports from the second source; and ECG structured findings, measurements, and 12-lead traces were extracted from the third source. ECGs were then labeled as detailed in the following sections, and ECGs without a label were discarded for all disease outcomes. Overall, 2,141,366 ECGs with at least 1 label from 461,466 patients were included (FIG. 1).

Specifically, FIG. 1 displays a block diagram of source data to dataset used for experiments described in this disclosure. First source (EHR) data was processed into a cardiovascular pipeline to retrieve patients with physical encounters in the first entity system or that have records of an ECG or Echocardiography study. The clinical database of data from the third source was processed into a database, such as a lightning memory-mapped (LMDB) database, of ECGs sampled at either 250 hz or 500 hz, having at least 8 leads, having an acquisition date stamp later than 1984, coming from patients older than 18 years (as reported in the ECG), and with a cross-referenced medical record number (checked against an EHR processed list from the first source). The no-label ECGs refer to ECGs that did not meet any labeling criteria (AS, AR, MS, MR, TR, EF<50%, nor IVS>15 mm).

Labeling

TTE-Confirmed Disease Outcome Definitions

A plurality of outcome labels (e.g., 7 outcome labels) were defined using TTE reports, one for each disease outcome of interest (AS, AR, MR, MS, TR, reduced EF, increased IVS thickness). String matching was used on the reports to identify the presence of valvular stenosis or regurgitation, as well as the associated severity level (Table 2). Specifically, Table 2 includes a keyword list for assigning an abnormality and severity to each valve in an Echocardiography report.

TABLE 1

| | List of inputs |
|---|---|
| Demographics and Vitals | Age (years), race (white/other), sex, smoke (ever), BMI (kg/m2), diastolic and systolic blood pressure (mmHg), heart rate (bpm), height (cm), weight (kg). |
| Labs | A1C (%), Bilirubin (mg/dl), BUN (mg/dl), Cholesterol (mg/dl), CKMB (ng/ml), Creatinine (mg/dl), CRP (mg/l), D dimer (mcg/ml FEU), Glucose (mg/dl), HDL (mg/dl), Hemoglobin (g/dl), LDH (u/l), LDL (mg/dl), Lymphocytes (%), Potassium (mmol/l), PRO BNP (pg/ml), Sodium (mmol/l), Troponin I and T (ng/ml), Triglyceride (mg/dl), Uric acid (mg/dl), VLDL (mg/dl), eGFR (ml/min/1.73 m$^2$) |
| ECG findings | Acute MI, Afib, Aflutter, Complete Block, Early rep, Fas block, First deg block, Intrav Block, In Lbbb, In rbbb, Ischemia, Lad, Lbbb, Low QRS, LVH, Non-spec ST, Non-spec T, Normal, Other Brady, PAC, Pacemaker, Poor tracing, Prior infarct, Prior MI anterior, Prolonged QT, PVC, RAD, RBBB, Sec deg block, Sinus Brady, SVT, Tachy, T Inversion, Vtach |
| ECG measurements | Avg RR interval (ms), PR interval (ms), P axis, QRS duration (ms), QT (ms), QTC (ms), R axis, T axis, Ventricular rate (bpm) |

TABLE 2

| | Abnormality |
|---|---|
| Stenosis | stenosis, stenotic |
| Regurgitation | regurgitation, regurgitant, insufficiency |

Severity

| | |
|---|---|
| Normal | absent, no stenosis, no AS, no MS, not stenotic, no PS, no tricuspid stenosis, no significant, no regurgitation, No TR, No MR, TS excluded, MS excluded, AS excluded, w/o stenosis, no mitral, no AR, trace, no evidence of, no pulmonic, no mitral, without aortic stenosis, stenosis is absent, no mitral regurgitation, physiologic, no hemodynamically, Normal 2-D, Normal MV, not sign, Normal structure and function, normal prosthetic, normal function, function normal, There is a normal amount of, is probably normal, is normal without |
| Mild | mild, valvular, aortic stenosis is present, valve stenosis is present, stenosis is possible, stenosis is possibly present, borderline |
| Moderate | moderate, Mod |
| Severe | severe, possibly, severe, moderate-severe, mod-severe, moderate - severe, moderately severe, moderate to severe, critical, consistent with significant |

Valve

| | |
|---|---|
| Aortic | aortic, AS, AR, AV |
| Tricuspid | tricuspid, TR, TS, TV |
| Mitral | mitral, MR, MS, MV |

Each of 5 valvular conditions of interest were labeled as positive if moderate or severe and negative if reported normal or mild in severity, or a missing label was otherwise assigned.

Reduced EF was defined as a TTE-reported EF of <50%, and increased IVS thickness as >15 mm, although it will be appreciated that other ranges for EF and/or IVS thickness may be used to define reduced EF. TTEs not meeting those criteria were labeled as negative, and a missing label was assigned when the measurement was missing.

Outcome labels extracted from TTE reports for AS, AR, MR, MS, and TR were manually validated using chart review of 100-200 random samples where PPVs and negative predictive values (NPVs) of 98-100% were found.

ECG Labeling

Figure 2A:
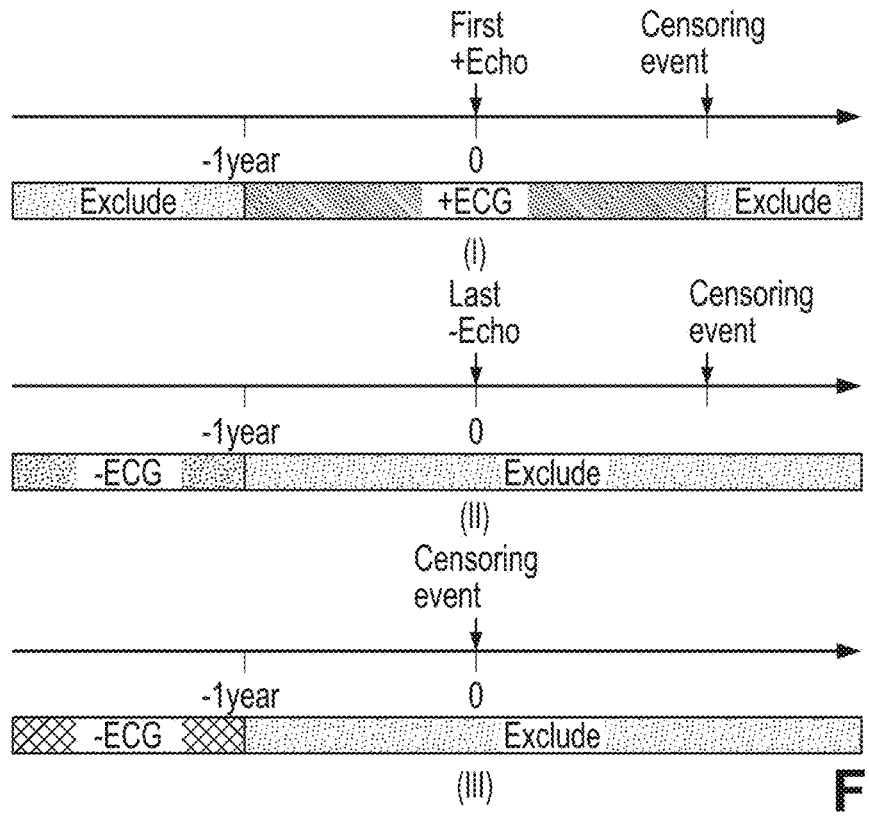
FIG. 2A is a patient timeline used to label (I) positive ECGs, (II) confirmed negative ECGs, and (III) unconfirmed negative ECGs.

An ECG was labeled as positive for a given outcome if it was acquired up to a first time period, e.g., one year, before or any time after (up to a censoring event) the patient's first positive TTE report. An ECG was labeled as negative if it was acquired more than the first time period, e.g., one year, prior to the last negative TTE or a censoring event without any prior positive TTEs (FIG. 2A). Specifically, FIG. 2A displays the patient timeline used to label (I) positive ECGs (+ECG in plot I), (II) confirmed negative ECGs (-ECG in plot II), and (III) unconfirmed negative ECGs (-ECG in plot III). The censoring event in plots I and II in FIG. 2A are any intervention that could modify the underlying physiology of the disease of interest. The last negative Echo ensures no record of prior positive Echo exists. The bottom timeline is used for patients that never got an Echo. The censoring event in plot III in FIG. 2A is defined as the last known patient encounter where physical presence is required.

Also, in the absence of any history of TTE, an ECG was also classified as negative if there was at least 1 year of subsequent follow-up without a censoring event and no coded diagnoses for the relevant disease (Table 3). Specifically, Table 3 lists ICD-10 codes used to search for evidence of diagnosis in ECGs from patients that never had an Echo. A negative label was assigned if none of the codes were ever present in the patient's chart.

TABLE 3

| Diagnosis | ICD10 codes |
|---|---|
| AS | I06.0, I06.2, I06.8, I06.9, I08.0, I08.2, I08.3, I08.8, I08.9, I35.0, I35.2, I35.8, I35.9, Z95.4, I33.*, Q20.*, Q21.*, Q22.*, Q23.*, Q24.* |
| AR | I06.1, I06.2, I06.8, I06.9, I08.0, I08.2, I08.3, I08.8, I08.9, I35.1, I35.2, I35.8, I35.9, Z95.4, I33.*, Q20.*, Q21.*, Q22.*, Q23.*, Q24.* |
| MR | I05.1, I05.2, I05.8, I05.9, I08.0, I08.1, I08.3, I08.8, I34.0, I34.1, I34.8, I34.9, Z95.4, I33.*, Q20.*, Q21.*, Q22.*, Q23.*, Q24.* |
| MS | I05.0, I05.2, I05.8, I05.9, I08.0, I08.1, I08.3, I08.8, I34.2, I34.8, I34.9, Z95.4, I33.*, Q20.*, Q21.*, Q22.*, Q23.*, Q24.* |
| TR | I07.1, I07.2, I07.8, I07.9, I08.1, I08.2, I08.3, I08.8, I36.1, I36.2, I36.8, I36.9, Z95.4, I33.*, Q20.*, Q21.*, Q22.*, Q23.*, Q24.* |
| EF < 50% | I42.0, I42.6, I42.7, I42.8, I42.9, T86.2, T86.3, Z94.1, Z94.3, I09.81, I97.13, I25.5, B33.2, O90.3, I43.*, I50.*, I51.8* |
| IVS > 15 mm | I37.1, I37.2, Z95.4, E83.11, I10.*, I11.*, I12.*, I13.*, I15.*, I16.*, E85.*, I42.1*, I42.2*, Q20.*, Q21.*, Q22.*, Q23.*, Q24.*, Q25.*, E74.*, E75.*, D86.* |

A censoring event was defined as death, end of observation, or an intervention that directly treated the disease and could modify the underlying physiology or impact the ECG signal, such as valve replacement or repair. In other embodiments, heart transplant or LVAD status, for example, may be included as censoring events. A negative TTE report after a positive TTE report also may be used as a censoring event to account for the possibility of such interventions being performed outside of the first entity system.

For the composite endpoint, an ECG was labeled as positive if any of the seven individual outcomes were positive and as negative if all seven outcomes were negative.

Model Development

A plurality of models, e.g., 7 models, may be developed using different combinations of multiple input sets including structured data (demographics, vitals, labs, structured ECG findings and measurements) and ECG voltage traces.

In one instance, for the ECG trace models, a low-parameter convolutional neural network (CNN) was developed with 18,495 trainable parameters that consisted of six 1D CNN-Batch Normalization-ReLU (CBR) layer blocks followed by a two-layer multilayer perceptron and a final logistic output layer (Table 4). Specifically, Table 4 details a single output low-parameter CNN design for training on 8 non-derived ECG leads. The network contains a total of 18,945 trainable and 384 non-trainable parameters. Both Dropout layers were set at 25% drop rate. CBR is a brief notation for a sequence of 1D CNN, batch normalization, and ReLU layers.

TABLE 4

| Layer | Output Shape | #Parameters |
| --- | --- | --- |
| Input | (5000, 8) | 0 |
| Rescaling | (5000, 8) | 0 |
| CBR-1 | (5000, 16) | 656 + 64 |
| CBR-2 | (5000, 16) | 1,296 + 64 |
| MaxPool1D | (1666, 16) | 0 |
| CBR-3 | (1666, 16) | 1,296 + 64 |
| CBR-4 | (1666, 16) | 1,296 + 64 |
| MaxPool1D | (555, 16) | 0 |
| CBR-5 | (555, 16) | 1,296 + 64 |
| CBR-6 | (555, 16) | 1,296 + 64 |
| MaxPool1D | (185, 16) | 0 |
| CBR-7 | (185, 16) | 1,296 + 64 |
| CBR-8 | (185, 16) | 1,296 + 64 |
| MaxPool1D | (61, 16) | 0 |
| CBR-9 | (61, 16) | 1,296 + 64 |
| CBR-10 | (61, 16) | 1,296 + 64 |
| MaxPool1D | (20, 16) | 0 |
| CBR-11 | (20, 16) | 1,296 + 64 |
| CBR-12 | (20, 16) | 1,296 + 64 |
| MaxPool1D | (6, 16) | 0 |
| Flatten | (96,) | 0 |
| Dense + Dropout | (32,) | 3104 |
| Dense + Dropout | (16,) | 528 |
| Dense | (1,) | 17 |

Figure 2B:
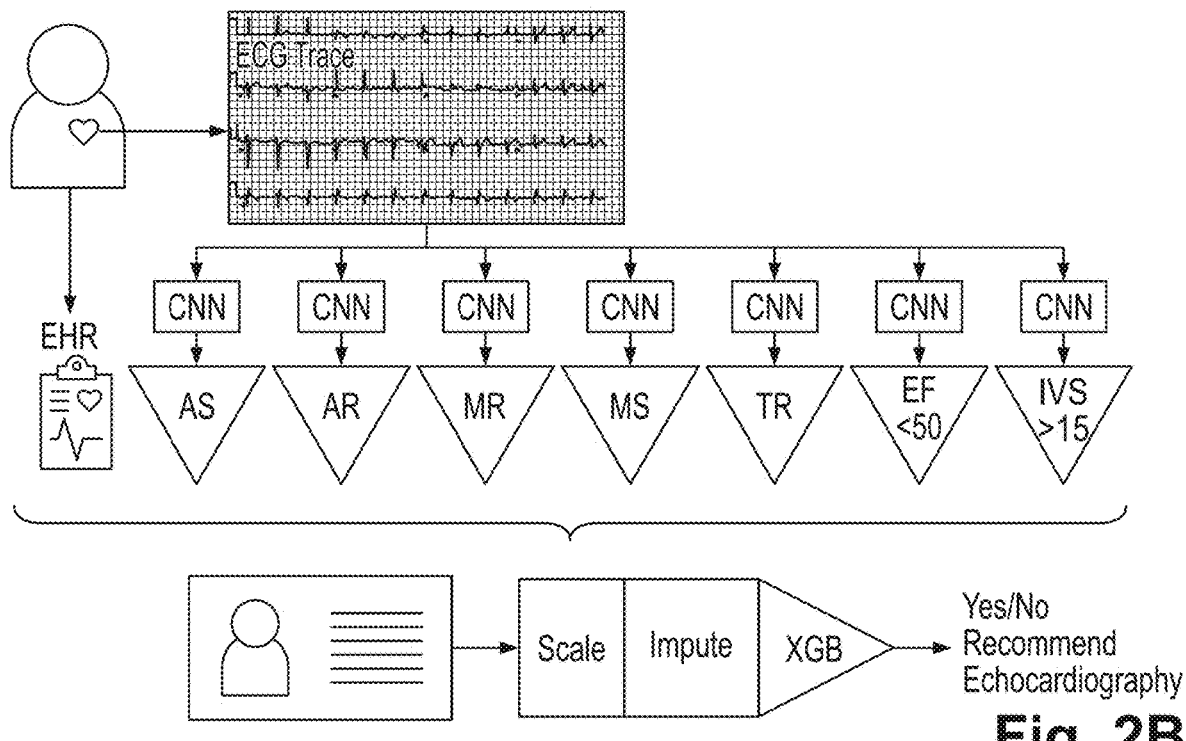
FIG. 2B is a block diagram for a composite model that shows the classification pipeline for ECG trace and other EHR data.

Each CNN layer consisted of 16 kernels of size 5. The same network configuration was used to train one model per clinical outcome, resulting in 7 independently trained CNN models (FIG. 2B). Specifically, FIG. 2B displays a block diagram for a composite model that shows the classification pipeline for ECG trace and other EHR data. The output of each neural network (the triangles in FIG. 2B) applied to ECG trace data is concatenated to labs, vitals, and demographics to form a feature vector. The vector is the input to a classification pipeline (min-max scaling, mean imputation, and XGBoost classifier), which outputs a recommendation score for the patient.

To form the final composite model and combine ECG trace-based models with structured data, the risk scores resulting from the individual CNNs were concatenated with the structured data. The concatenated feature vector was used to train a classification pipeline consisting of a min-max scaler (min 0, max 1), mean imputation, and a machine learning model or gradient boosting library classifier such as an XGBoost classifier, as shown in FIG. 2B.

Model Evaluation. The models were evaluated using two approaches, 1) a traditional random cross-validation partition, and 2) a retrospective deployment scenario where, using 2010 as the simulated deployment year, past data was used to train and future data was used to test. Area under receiver operating characteristic curve (AUROC), area under the precision-recall curve (AUPRC), and other performance metrics (sensitivity, specificity, positive and negative predictive values) were measured at multiple operating points (Youden, F1, F2, at 90% and 50% sensitivity, at 25% and 33% PPV).

Cross-validation. A 5-fold cross-validation was followed by randomly sampling 5 mutually exclusive sets of patients. Each set was expanded to all ECGs from each patient to form the training and test ECG sets. When training the CNN models for each individual endpoint, samples with missing labels were discarded. The model was then applied to all test samples—regardless of missingness of the true label—and marginal performance was evaluated only on samples with complete labels that also satisfied the composite model labeling criteria described above. Performance statistics were reported as the average across the five folds (with a 95% confidence interval) in a random ECG per patient.

Retrospective deployment. In addition to the cross-validation approach, a deployment of the model was also retrospectively simulated using a cutoff of the year 2010, re-labeling all ECGs with information available as of Jan. 1, 2010. This artificially constrained dataset was used to replicate the cross-validation experiments and train a deployment model using data prior to 2010. The deployment model then was applied to the first ECG per patient for all patients seen through Dec. 31, 2010. Performance statistics on all ECGs from patients at risk were measured, and the true outcomes of the at-risk population using all information available as of May 4, 2021, were determined.

Results from Example 1

568,802 TTE reports were identified from 277,358 patients, of which 150,730 were positive for at least one disease outcome label. Disease prevalence ranged from 0.7% for MS to 19.9% for reduced EF (Table 5). Specifically, Table 5 lists TTE label count and relative prevalence for each diagnosis among the 568,802 TTEs.

TABLE 5

|  | Normal-Mild | Moderate-Severe | Prevalence |
| --- | --- | --- | --- |
| AS | 271,384 | 21,790 | 7.4% |
| AR | 278,439 | 13,878 | 4.7% |
| MR | 270,266 | 32,002 | 10.6% |
| MS | 302,649 | 2,188 | 0.7% |
| TR | 258,236 | 36,069 | 12.3% |
|  | False | True |  |
| EF < 50 | 308,695 | 76,806 | 19.9% |
| IVS > 15 | 362,974 | 27,389 | 7.0% |

2,141,366 ECGs were identified from 461,466 patients who met criteria for a positive or negative individual disease label (AS, AR, MS, MR, TR, EF, or IVS), of which 1,378,832 ECGs from 333,128 patients qualified for the composite label (Table 6). Specifically, Table 6 lists the count of ECGs and total prevalence for each diagnosis among the 2,141,366 ECGs with at least a complete label. Confirmed counts are based on ECGs from patients that also underwent an Echocardiography study that confirmed the diagnosis. Unconfirmed negatives (–) show the count of ECGs from patients that never got an Echocardiography and had no history of the disease using the ICD code filters from Table 3.

TABLE 6

|  | Negative | Positive | Prevalence | No label |
|---|---|---|---|---|
| AS | 1,608,160 | 65,037 | 3.9% | 468,169 |
| AR | 1,609,710 | 58,209 | 3.5% | 473,447 |
| MR | 1,536,378 | 145,355 | 8.6% | 459,633 |
| MS | 1,691,737 | 9,920 | 0.6% | 439,709 |
| TR | 1,556,020 | 148,916 | 8.7% | 436,430 |
| EF < 50% | 1,375,507 | 315,874 | 18.7% | 449,985 |
| IVS > 15 mm | 1,235,255 | 121,583 | 9.0% | 784,528 |
| Present Composite Model | 805,353 | 573,479 | 41.6% | 762,534 |

Table 7 displays a breakdown by ECG label of each model feature. Specifically, Table 7 displays average value for each predictor grouped by whether they qualified for the composite labeled ECGs. False refers to ECGs from patients that were not diagnosed with any of the 7 diseases within a year, and True to ECGs from patients that were diagnosed with at least one of the 7 diseases within a year or before the ECG acquisition time.

TABLE 7

|  | FALSE | TRUE |
|---|---|---|
| Demographics and Vitals: |  |  |
| Age | 55.9 (16.9) | 71.2 (13.6) |
| Race | 96.9 | 97.5 |
| Sex | 44.7 | 58.3 |
| Smoker | 58.3 | 62.9 |
| BMI | 30.8 (8.4) | 30.1 (9.1) |
| BP Diastolic | 73.8 (11.2) | 70.2 (12.8) |
| BP Systolic | 127.5 (18.6) | 128.1 (21.5) |
| Heart Rate | 77.1 (14.8) | 76.1 (16.5) |
| Height | 168.3 (10.5) | 168.9 (11.2) |
| Weight | 87.2 (23.7) | 86.0 (24.5) |
| Labs: |  |  |
| A1C | 6.8 (3.9) | 6.9 (1.6) |
| BILI | 0.5 (0.5) | 0.6 (0.7) |
| BUN | 16.5 (8.7) | 25.6 (16.2) |
| Cholesterol | 183.6 (46.0) | 158.8 (47.4) |
| CKMB | 6.6 (23.5) | 10.0 (37.2) |
| Creatinine | 1.0 (2.0) | 1.4 (1.3) |
| CRP | 22.7 (51.0) | 48.3 (70.6) |
| Ddimer | 1.0 (2.0) | 1.9 (3.1) |
| Glucose | 114.0 (43.3) | 123.1 (52.1) |
| HDL | 49.6 (16.1) | 45.6 (15.6) |
| Hemoglobin | 13.7 (21.9) | 13.9 (43.9) |
| LDH | 217.4 (134.6) | 274.2 (290.8) |
| LDL | 103.4 (37.6) | 85.7 (37.1) |
| Lymphocytes | 24.9 (10.5) | 19.9 (10.6) |
| Potassium | 4.2 (0.7) | 4.3 (0.7) |
| PROBNP | 1032.1 (3880.0) | 6868.1 (12317.4) |
| Sodium | 139.3 (3.0) | 138.9 (3.7) |
| TroponinI | 0.8 (12.4) | 1.1 (10.2) |
| TroponinT | 0.1 (0.4) | 0.2 (1.1) |
| Triglyceride | 158.8 (127.7) | 144.9 (108.9) |

TABLE 7-continued

|  | FALSE | TRUE |
|---|---|---|
| UricAcid | 6.1 (2.1) | 7.1 (2.7) |
| VLDL | 30.4 (15.8) | 28.1 (15.9) |
| eGFR | 58.0 (16.9) | 49.8 (15.2) |
| ECG: |  |  |
| Avg RR Interval | 831.5 (186.0) | 794.2 (204.6) |
| PR Interval | 158.3 (32.6) | 175.5 (388.3) |
| P Axis | 47.7 (25.5) | 50.3 (36.4) |
| QRS Duration | 90.6 (17.7) | 109.6 (30.8) |
| QT | 392.3 (43.9) | 409.8 (59.5) |
| QTC | 433.5 (34.1) | 463.6 (45.9) |
| R Axis | 28.1 (40.7) | 17.9 (64.3) |
| T Axis | 42.6 (37.4) | 69.8 (69.8) |
| Vent Rate | 76.1 (18.8) | 80.8 (22.6) |
| Acute MI | 0.6 | 2 |
| AFIB | 3.1 | 18.4 |
| Normal | 52.6 | 28.4 |
| AFLUTTER | 0.6 | 2.8 |
| FAS Block | 1.9 | 4.9 |
| First Deg Block | 3.8 | 9.3 |
| Intrav Block | 0.8 | 5.2 |
| InRBBB | 0.1 | 0.9 |
| Ischemia | 5.4 | 18.3 |
| LAD | 5.7 | 14.8 |
| LBBB | 0.8 | 6.1 |
| LOWQRS | 3.5 | 6.2 |
| LVH | 5.7 | 10.6 |
| Non-Spec ST | 8.2 | 13.4 |
| Non-Spec T | 13.5 | 19.9 |
| PVC | 3.5 | 12.8 |
| PAC | 3.3 | 7 |
| Pacemaker | 1.3 | 10 |
| Poor Tracing | 4.1 | 6.5 |
| Prior Infarct | 12.5 | 28.6 |
| Prior MI Ant. | 4.6 | 12.2 |
| Prolonged QT | 3.2 | 8.4 |
| RAD | 1.9 | 3 |
| RBBB | 3.3 | 9.8 |
| Sinus Brady | 15.6 | 10.8 |
| Tachy | 7.9 | 7.9 |
| T Inversion | 2.7 | 7.5 |

At baseline, across 2.14 million ECGs, the median patient age was 64.7, 50.4% were male, and 96.7% were white (Table 8). Specifically, Table 8 lists features extracted at the time of the ECG and their overalls average, for continuous values, or prevalence, for binary values. Other ECG features not listed because of their rarity (<1%) were: Complete Block, Other Brady, Early Rep, IN LBBB, Sec Deg Block, SVT, and VTACH. ECG findings showed 43.5% were normal, 8.3% had atrial fibrillation, 1.0% showed acute myocardial infarction, and 7.7% showed left ventricular hypertrophy.

TABLE 8

|  | Mean | Median [IQR] |
|---|---|---|
| Demographics and Vitals: |  |  |
| Age (years) | 63 | 64.7 [52, 76] |
| Race (% White) | 96.7% |  |
| Sex (% Male) | 50.4% |  |
| Smoke (% Ever) | 59.1% |  |
| BMI (kg/m2) | 30.7 | 29.4 [25, 35] |
| Dias. BP (mmHg) | 72.6 | 72 [64, 80] |
| Sys. BP (mmHg) | 128.8 | 128 [116, 140] |
| Heart Rate (bpm) | 76.9 | 75 [66, 85] |
| Height (cm) | 168.6 | 167.6 [160, 178] |
| Weight (kg) | 87.2 | 84.1 [70, 100] |
| Labs: |  |  |
| A1C | 6.8 | 6.4 [5.7, 7.5] |
| BILI | 0.6 | 0.5 [0.3, 0.7] |

TABLE 8-continued

|  | Mean | Median [IQR] |
|---|---|---|
| BUN | 20.3 | 17 [13, 23] |
| Cholesterol | 171.6 | 167 [139, 199] |
| CKMB | 8.3 | 2.9 [1.8, 4.9] |
| Creatinine | 1.2 | 0.9 [0.8, 1.2] |
| CRP | 36.5 | 9 [2.5, 39.0] |
| D dimer | 1.5 | 0.6 [0.3, 1.5] |
| Glucose | 118.4 | 103 [93, 125] |
| HDL | 47.9 | 45 [37, 56] |
| Hemoglobin | 13.6 | 13.1 [11.6, 14.3] |
| LDH | 258 | 211 [173, 272] |
| LDL | 94.6 | 90 [68, 117] |
| Lymphocytes | 22.4 | 22 [14.8, 29] |
| Potassium | 4.2 | 4.2 [3.9, 4.5] |
| PROBNP | 4351 | 1015 [249, 3553] |
| Sodium | 139.2 | 140 [137, 141] |
| Troponin I | 88.8 | 3 [1.2, 5] |
| Troponin T | 13.5 | 1 [1, 3.8] |
| Triglyceride | 152.2 | 125 [89, 181] |
| Uric Acid | 6.6 | 6.2 [4.9, 7.9] |
| VLDL | 28.6 | 25 [18, 35] |
| eGFR | 54.5 | 60 [55.2, 60] |
| ECG: |  |  |
| Avg RR Interval | 813.5 | 806 [678, 938] |
| PR Interval | 164.4 | 160 [142, 180] |
| P Axis | 48.5 | 51 [34, 65] |
| QRS Duration | 97 | 90 [82, 102] |
| QT | 397.9 | 396 [366, 428] |
| QTC | 444.6 | 440 [419, 464] |
| R Axis | 22.9 | 21 [−9, 54] |
| T Axis | 51.6 | 45 [23, 70] |
| Vent Rate | 78.2 | 74 [64, 88] |
| Acute MI | 1.0% |  |
| AFIB | 8.3% |  |
| Normal | 43.5% |  |
| AFLUTTER | 1.3% |  |
| FAS Block | 3.2% |  |
| First Deg Block | 6.1% |  |
| Intrav Block | 2.1% |  |
| INRBBB | 3.3% |  |
| Ischemia | 9.6% |  |
| LAD | 9.1% |  |
| LBBB | 2.6% |  |
| LOWQRS | 4.7% |  |
| LVH | 7.7% |  |
| Non-Spec ST | 10.4% |  |
| Non-Spec T | 16.0% |  |
| PVC | 6.7% |  |
| PAC | 5.1% |  |
| Pacemaker | 4.2% |  |
| Poor Tracing | 5.3% |  |
| Prior Infarct | 18.4% |  |
| Prior MI Ant. | 7.3% |  |
| Prolonged QT | 5.0% |  |
| RAD | 2.2% |  |
| RBBB | 6.0% |  |
| Sinus Brady | 13.5% |  |
| Tachy | 8.4% |  |
| T Inversion | 4.5% |  |

Composite Model Input Evaluation

Table 9 shows the results of 5-fold cross validation comparing composite model performance as a function of different input features. Specifically, Table 2 provides a performance comparison of cross-validated models with varying input features for the composite endpoint (valve disease, reduced EF, increased IVS). All values are shown in percentage with the 95% CI in between brackets. Each model was tested on a random ECG per patient. The AUROC ranged from 84.7 [95% CI: 84.5,85.0] for the model built only with structured ECG findings and measurements to 93.2 [93.0,93.4] for the model with all available inputs (structured ECG findings and measurements, demographics, labs, vitals, and ECG traces). While the model with all available inputs provided the best performance, the remainder of the results focus on models that include only age, sex, and ECG traces since this input set is readily available from the third entity or other ECG systems and best balances portability and performance.

TABLE 9

| Input | ROC-AUC | PRC-AUC | PPV@90% Sens. | Spec.@90% Sens. |
|---|---|---|---|---|
| A) ECG Findings and Meas. | 84.7 [84.5, 85.0] | 67.5 [67.0, 67.9] | 36.1 [35.7, 36.5] | 52.8 [52.0, 53.6] |
| B) Demo., Labs, and Vitals | 87.9 [87.7, 88.1] | 72.9 [72.4, 73.4] | 43.0 [42.8, 43.1] | 64.4 [64.2, 64.6] |
| C) ECG Traces | 91.0 [90.7, 91.4] | 77.6 [76.8, 78.5] | 50.8 [49.8, 51.7] | 74.0 [73.0, 74.9] |
| A + C | 91.3 [91.0, 91.5] | 78.3 [77.5, 79.1] | 51.5 [50.7, 52.3] | 74.7 [74.0, 75.5] |
| Age + Sex + C | 91.4 [91.1, 91.7] | 77.5 [76.6, 78.5] | 52.2 [51.3, 53.0] | 75.5 [74.7, 76.2] |
| A + B | 91.5 [91.4, 91.7] | 79.7 [79.1, 80.2] | 51.6 [51.0, 52.1] | 74.8 [74.3, 75.3] |
| B + C | 93.1 [92.8, 93.3] | 82.7 [82.1, 83.3] | 57.0 [56.1, 58.0] | 79.8 [79.1, 80.5] |
| A + B + C | 93.2 [93.0, 93.4] | 83.0 [82.5, 83.5] | 57.5 [56.3, 58.6] | 80.1 [79.3, 81.0] |

Cross-Validation Performance of Composite Model

The composite model with age, sex, and ECG traces as inputs yielded an AUROC of 91.4 [91.1, 91.7] and a PPV of 52.2% [51.3, 53.0] at 90% sensitivity (Table 10). Specifically, Table 10 displays ECG traces only model results for cross-validation experiments. Results are shown at a random ECG per patient and averaged across 5 folds. All values are shown in percentage with the 95% CI in between brackets.

TABLE 10

|  | Prevalence | ROC-AUC | PRC-AUC | PPV@90% Sens. | Spec.@90% Sens. |
|---|---|---|---|---|---|
| AS | 3.7 [3.6, 3.8] | 92.4 [92.0, 92.8] | 35.0 [32.4, 37.8] | 14.7 [13.9, 15.6] | 80.1 [78.8, 81.3] |
| AR | 2.9 [2.8, 2.9] | 87.5 [87.0, 88.0] | 21.1 [19.1, 23.2] | 7.2 [6.9, 7.5] | 65.9 [63.8, 67.9] |
| MR | 6.9 [6.8, 7.0] | 92.2 [91.8, 92.6] | 51.9 [50.0, 53.8] | 24.2 [22.7, 25.6] | 79.0 [77.4, 80.5] |
| MS | 0.4 [0.4, 0.5] | 92.3 [90.5, 93.8] | 7.2 [4.9, 10.5] | 2.1 [1.4, 3.0] | 80.7 [72.5, 86.9] |
| IR | 7.3 [7.2, 7.3] | 92.6 [92.0, 93.1] | 57.2 [55.6, 58.7] | 26.0 [24.3, 27.7] | 79.9 [78.1, 81.6] |

TABLE 10-continued

| | Prevalence | ROC-AUC | PRC-AUC | PPV@90% Sens. | Spec.@90% Sens. |
|---|---|---|---|---|---|
| EF < 50% | 13.0 [12.8, 13.1] | 93.0 [92.3, 93.6] | 70.5 [66.1, 74.5] | 41.3 [38.4, 44.2] | 80.9 [78.6, 83.0] |
| IVS > 15 mm | 6.2 [6.1, 6.3] | 89.1 [88.9, 89.3] | 36.7 [35.6, 37.8] | 17.1 [16.6, 17.6] | 71.2 [70.4, 72.0] |
| Present Composite Model With Age, Sex, and ECG Traces as inputs | 22.9 [22.8, 23.1] | 91.4 [91.1, 91.7] | 77.5 [76.6, 78.5] | 52.2 [51.3, 53.0] | 75.5 [74.7, 76.2] |

Figure 3:
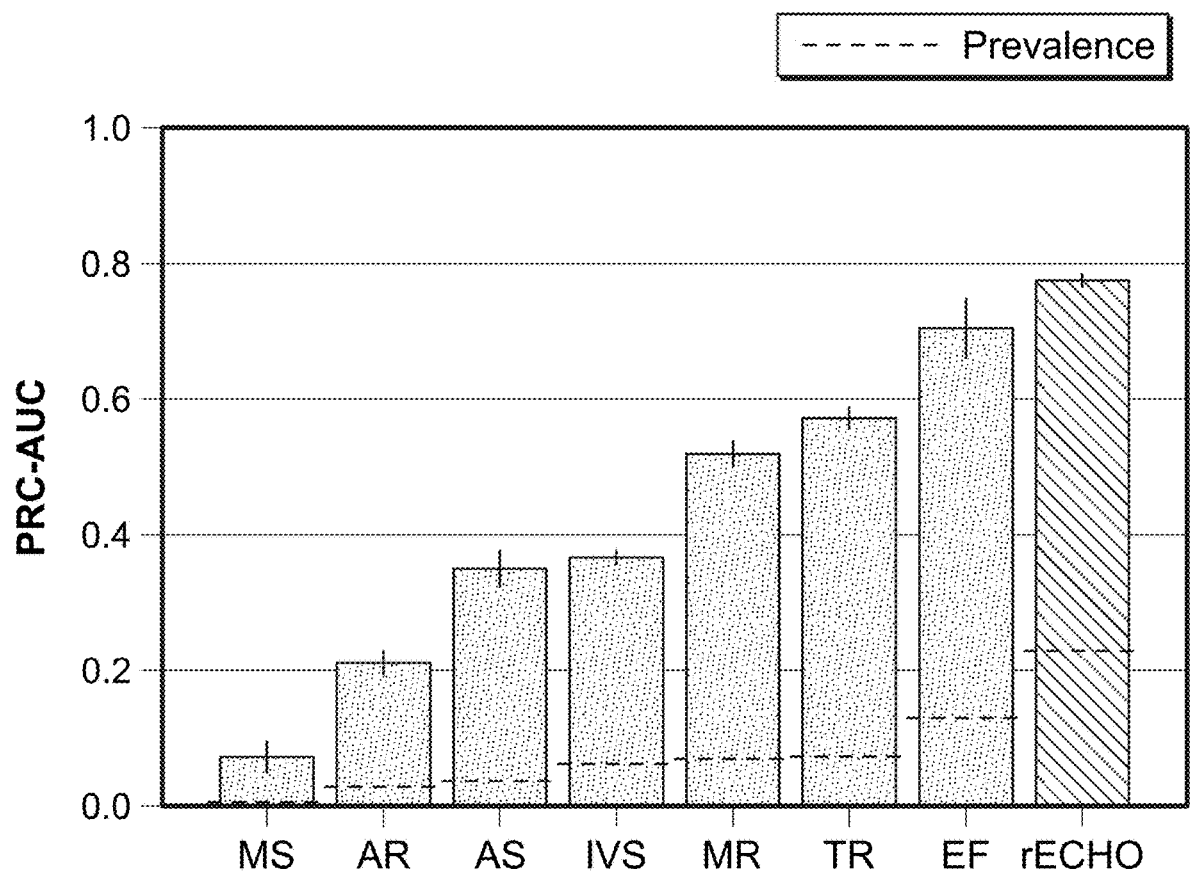
FIG. 3 is a display of an area under a Precision-Recall curve for each of a plurality of individual diseases according to a model of the present disclosure.

The composite model yielded a significantly higher PPV than any of the 7 models trained for an individual component endpoint, with the individual model PPVs ranging from 2.1% [1.4, 3.0] for MS to 41.3% [38.4, 44.2] for reduced EF (Table 10). The same trend was found for the AUPRC of the composite model, which was 77.5% [76.6, 78.5], compared to the individual models ranging from 7.2% [4.9, 10.5] for MS to 70.5% [66.1, 74.5] for EF (FIG. 3). Specifically, FIG. 3 displays an area under the Precision-Recall curve for each of the individual diseases and the model of the present disclosure. The dashed line shows the prevalence for each of the labels.

Performance metrics for alternate composite model operating points are presented in Table 11. Specifically, Table 11 lists composite model performance metrics at multiple threshold values.

TABLE 11

| Threshold | NPV | PPV | Sensitivity | Specificity | Value |
|---|---|---|---|---|---|
| 0.1 | 95.8 [95.7, 95.9] | 54.4 [53.7, 55.2] | 88.5 [88.1, 88.8] | 78.0 [77.4, 78.5] | 0.1 |
| 0.2 | 92.8 [92.6, 93.0] | 68.1 [67.4, 68.8] | 76.9 [76.1, 77.6] | 89.3 [89.0, 89.6] | 0.2 |
| 0.3 | 90.3 [90.0, 90.5] | 75.9 [75.2, 76.6] | 66.0 [64.9, 67.1] | 93.8 [93.6, 93.9] | 0.3 |
| 0.4 | 87.6 [87.4, 87.8] | 81.4 [80.6, 82.3] | 54.1 [53.3, 54.8] | 96.3 [96.1, 96.5] | 0.4 |
| 0.5 | 84.8 [84.7, 85.0] | 85.9 [84.9, 86.8] | 41.1 [40.6, 41.5] | 98.0 [97.8, 98.1] | 0.5 |
| 0.6 | 82.3 [82.0, 82.5] | 89.3 [88.5, 90.1] | 28.2 [26.6, 29.9] | 99.0 [98.9, 99.1] | 0.6 |
| 0.7 | 79.8 [79.3, 80.3] | 91.6 [91.0, 92.2] | 15.0 [11.6, 19.3] | 99.6 [99.5, 99.7] | 0.7 |
| 0.8 | 77.8 [77.5, 78.0] | 94.2 [92.6, 95.5] | 3.5 [1.6, 7.4] | 99.9 [99.9, 100.0] | 0.8 |
| 0.9 | 77.1 [76.9, 77.2] | 0.0 [0.0, 100.0] | 0.0 [0.0, 0.0] | 100.0 [100.0, 100.0] | 0.9 |
| Youden | 94.4 [94.2, 94.6] | 61.6 [60.2, 63.0] | 83.2 [82.6, 83.9] | 84.6 [83.6, 85.5] | 14.4 [13.5, 15.3] |
| F1 | 92.5 [92.1, 92.9] | 69.4 [67.2, 71.6] | 75.5 [73.8, 77.2] | 90.1 [88.8, 91.2] | 21.4 [19.6, 23.3] |
| F2 | 95.9 [95.7, 96.0] | 54.1 [53.3, 54.9] | 88.7 [88.2, 89.2] | 77.6 [76.7, 78.4] | 9.8 [9.2, 10.4] |
| @25% PPV | 99.5 [99.4, 99.6] | 25.0 [25.0, 25.0] | 99.8 [99.7, 99.9] | 10.9 [10.2, 11.5] | 0.7 [0.6, 0.8] |
| @33% PPV | 98.8 [98.7, 98.9] | 33.0 [33.0, 33.0] | 98.3 [98.2, 98.5] | 40.6 [40.1, 41.0] | 2.2 [2.1, 2.4] |
| @90% Spec. | 92.5 [92.3, 92.8] | 69.2 [68.8, 69.6] | 75.6 [74.5, 76.6] | 90.0 [90.0, 90.0] | 21.2 [20.7, 21.6] |
| @50% Sens. | 86.7 [86.6, 86.8] | 83.0 [81.9, 84.1] | 50.0 [50.0, 50.0] | 97.0 [96.7, 97.2] | 43.3 [42.7, 43.8] |
| @90% Sens. | 96.2 [96.2, 96.2] | 52.2 [51.3, 53.0] | 90.0 [90.0, 90.0] | 75.5 [74.7, 76.2] | 8.9 [8.6, 9.2] |

Simulated Deployment Performance of Composite Model

As of Jan. 1, 2010, 563,375 ECGs were identified with a qualifying label for any of the seven clinical outcomes prior to 2010, of which 349,675 ECGs qualified for the composite label to train the deployment model. A "qualifying" label was one that met the criteria for the applicable outcome label. A cross-validation experiment within this data subset showed similar, yet slightly reduced performance of the composite model compared with the full dataset (AUROC 88.8 [88.5, 89.1]; PPV=44.0% [42.9, 45.1] at 90% sensitivity; Table 12). Specifically, Table 12 lists cross-validation performance metrics computed with data prior to 2010. The five-fold average threshold that yielded 90% Sensitivity (0.056 from a range of 0 to 1) was taken to produce binary predictions on the deployment model.

TABLE 12

| | Prevalence | ROC-AUC | PRC-AUC | PPV@90% Sens. | Spec.@90% Sens. |
|---|---|---|---|---|---|
| AS | 2.5 [2.3, 2.6] | 90.6 [89.7, 91.4] | 22.8 [19.0, 27.1] | 8.1 [7.4, 8.9] | 74.1 [71.5, 76.5] |
| AR | 2.8 [2.7, 2.9] | 84.5 [83.5, 85.5] | 15.6 [14.2, 17.1] | 6.1 [5.6, 6.6] | 60.1 [55.6, 64.5] |
| MR | 7.0 [6.8, 7.3] | 89.3 [88.2, 90.2] | 40.1 [36.0, 44.2] | 19.6 [17.6, 21.7] | 72.0 [68.6, 75.2] |
| MS | 0.3 [0.2, 0.3] | 88.1 [84.3, 91.1] | 3.8 [1.8, 7.7] | 0.7 [0.4, 1.2] | 65.0 [46.6, 79.7] |
| TR | 5.4 [5.2, 5.6] | 90.6 [89.9, 91.2] | 41.2 [38.3, 44.1] | 16.7 [15.3, 18.1] | 74.3 [71.6, 76.8] |
| EF < 50% | 12.3 [12.0, 12.6] | 90.7 [87.7, 93.0] | 57.5 [46.7, 67.7] | 35.6 [30.2, 41.4] | 77.1 [71.0, 82.3] |
| IVS > 15 mm | 7.2 [7.1, 7.4] | 85.9 [85.1, 86.7] | 32.4 [31.4, 33.5] | 16.3 [15.1, 17.6] | 64.1 [60.6, 67.5] |
| Composite Model | 21.1 [20.9, 21.3] | 88.8 [88.5, 89.1] | 67.6 [66.3, 68.9] | 44.0 [42.9, 45.1] | 69.4 [68.0, 70.8] |

The deployment dataset contained ECGs from 69,465 patients (FIG. 4). Of these, 5,730 patients were diagnosed with one of the seven clinical outcomes prior to 2010. This resulted in 63,735 at-risk patients identified between January 1 and December 31 of 2010. Using the previously determined threshold noted above, the deployment model labeled 22.2% of patients as high risk for any of the seven disease outcomes and 77.8% of patients as not high risk. Among the 4,642 predicted high-risk patients with adequate follow-up who met defined criteria for the composite label, 1,867 patients truly developed one of the outcomes, yielding a PPV of 40.2%. Of these 1,867 patients, 231 (12.4%) developed AS, 147 (7.9%) developed AR, 562 (30.1%) developed MR, 32 (1.7%) developed MS, 505 (27%) developed TR, 1074 (57.5%) developed low EF, and 460 (24.6%) developed IVS thickening—noting that 1083 developed 1 of the 7 diseases while 496 developed 2, 225 developed 3, 55 developed 4, 7 developed 5, 1 developed 6, and 0 developed all 7 diseases.

Figure 4A:
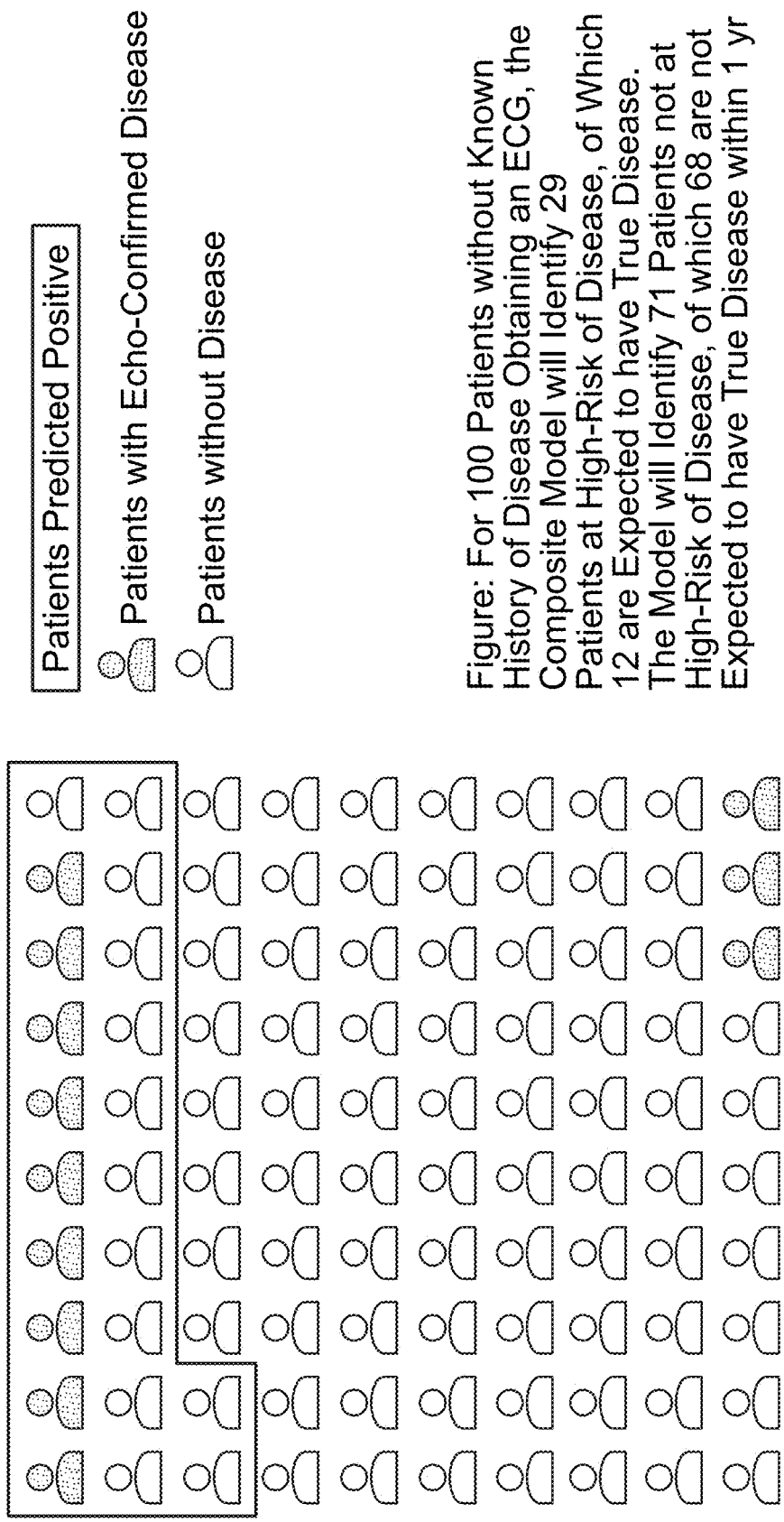
FIG. 4A displays patient-level retrospective deployment results for a deployment dataset according to one aspect of the disclosure.
Figure 4B:
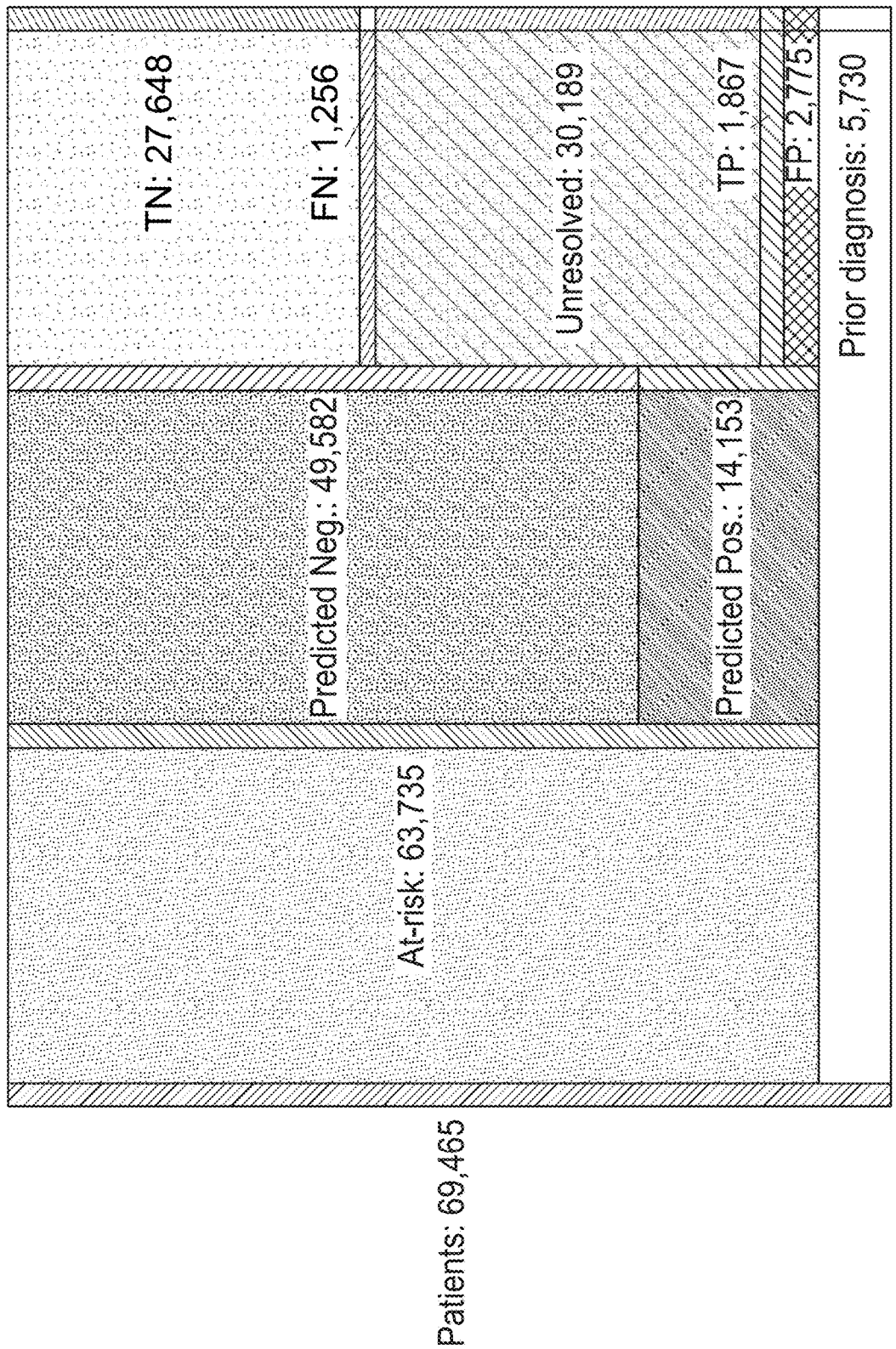
FIG. 4B displays a Sankey plot of retrospective deployment results for the deployment dataset related to FIG. 4A.

Among those predicted not high risk, 27,648 patients did not develop any of the outcomes within a year, for an NPV of 95.7%. At the patient level, for every 100 at-risk patients who obtained an ECG, the model used with the present system and methods would identify 22 as high-risk, of which 9 would truly have disease, and 78 as not-high risk, of which 75 would truly not have disease within 1 year (FIG. 4A). Specifically, FIG. 4A displays patient-level retrospective deployment results from 2010 according to the present composite model. FIG. 4B displays a Sankey plot of retrospective deployment results.

Outcome labels for 30,335 patients were undefined due to inadequate follow-up or patients not meeting defined criteria for the composite label, as noted above. However, baseline characteristics among these undefined patients and patients with complete outcome labels were similar (Table 13). Specifically, Table 13 displays baseline characteristics of patients with resolved vs unresolved labels in deployment scenario. The AUROC among resolved labels was 84.4.

TABLE 13

|  | Resolved | | Unresolved | |
| --- | --- | --- | --- | --- |
|  | Mean(SD) | Median | Mean(SD) | Median |
| Age | 56 (17) | 57 | 63 (17) | 64 |
| BMI | 31 (8) | 29 | 31 (8) | 30 |
| BP Diastolic | 73 (11) | 72 | 74 (12) | 73 |
| BP Systolic | 127 (18) | 124 | 130 (19) | 128 |
| Heart Rate | 76 (13) | 74 | 75 (14) | 74 |
| Height | 168 (10) | 168 | 168 (11) | 168 |
| Weight | 87 (23) | 84 | 87 (25) | 84 |
| A1C | 7 (1) | 6 | 7 (1) | 6 |
| BILI | 1 (1) | 0 | 1 (1) | 0 |
| BUN | 17 (9) | 15 | 19 (11) | 17 |
| Cholesterol | 182 (43) | 178 | 178 (43) | 173 |
| CKMB | 4 (8) | 3 | 5 (10) | 3 |
| Creatinine | 1 (1) | 1 | 1 (1) | 1 |
| CRP | 17 (40) | 4 | 21 (45) | 5 |
| Ddimer | 1 (3) | 0 | 2 (3) | 1 |
| Glucose | 109 (36) | 99 | 111 (36) | 100 |
| HDL | 51 (16) | 48 | 50 (15) | 48 |
| Hemoglobin | 14 (28) | 14 | 15 (50) | 13 |
| LDH | 217 (106) | 191 | 246 (239) | 197 |
| LDL | 102 (36) | 98 | 98 (35) | 94 |
| Lymphocytes | 25 (10) | 25 | 24 (11) | 23 |
| Potassium | 4 (0) | 4 | 4 (0) | 4 |
| PROBNP | 2408 (8570) | 418 | 1577 (2868) | 483 |
| Sodium | 139 (3) | 139 | 139 (3) | 139 |
| Troponin1 | 0 (0) | 0 | 0 (1) | 0 |
| TroponinT | 0 (0) | 0 | 0 (0) | 0 |
| Triglyceride | 150 (105) | 126 | 151 (115) | 127 |

TABLE 13-continued

|  | Resolved | | Unresolved | |
| --- | --- | --- | --- | --- |
|  | Mean(SD) | Median | Mean(SD) | Median |
| UricAcid | 6 (2) | 6 | 7 (3) | 6 |
| VLDL | 30 (15) | 27 | 24 (11) | 23 |
| eOFR | 58 (8) | 60 | 56 (9) | 60 |

The composite model described in Example 1 with results of 91.4% AUROC, 52.2% PPV and 90% sensitivity on cross-validation is based on age, sex, and ECG traces alone as inputs, which may represent one possible favorable balance between performance and portability. This model uses data readily available from any ECG system, including those systems commonly available to and/or recognized by those of ordinary skill in the art, so that it can easily be deployed across most healthcare systems. Although the model substantially outperformed those using only demographics or structured ECG findings and measurements, it will be appreciated that other demographics/vitals, labs, ECG findings, and/or ECG measurements, including any of the options listed in Table 1 or other relevant options may be used as inputs to train and/or deploy the composite model. While the addition of EHR data did slightly improve performance, the inclusion of EHR data in some instances may result in decreased portability with the need for EHR or clinical data warehouse integration. Thus, implementation of the present composite model may represent a balance between marginal improvements in performance due to the inclusion of different or additional inputs versus the time or processing costs associated with the integration, normalization, structuring, and/or other processing of additional or alternative inputs.

In a simulated retrospective deployment on ECGs from 2010, approximately 22% of at-risk patients without history of disease were predicted to be high-risk for diagnosis of one of the seven cardiovascular disease outcomes within the following year. Of the patients who were predicted high risk and had adequate follow-up, over 40% were truly diagnosed with disease in the following year after index ECG, through only standard clinical care at the time and without any potential clinician behavior change or active intervention that true deployment of such a prediction model or decision support tool may elicit. This suggests that this 40% PPV is most likely a lower bound for the expected real-world performance of the composite model described in Example 1. Meanwhile the 95.7% NPV suggests that little disease will be missed, but even in this case, the model would not change what would otherwise be the clinical course for these patients. Clinician behavior may change with a negative prediction if they are falsely reassured that the patient does not have disease or changes their pretest probability and clinical reasoning. Thus, implementation can be designed so that clinicians are only alerted when a patient is predicted to be high risk, and for those patients, the real-world data discussed herein indicates that more than 4 out of every 10 patients will have true disease. Cross-validation performance metrics that depend on prevalence (PPV, NPV, and AUPRC) may overestimate real-world performance given the lower incidence or prevalence across the generally smaller time window of deployment as opposed to the typically extensive period used in cross-validation. For example, PPV in cross-validation of the model disclosed herein was 52% but dropped to 40% in simulated deployment. However, even a 40% increase in the identification and potential for treatment of patients that ultimately experience one or more of the modeled disease states still represents a marked-improvement over situations in which the disease states are not identified until later on, e.g., once the patient has begun experiencing symptoms.

The exemplary composite model described in Example 1 has some characteristics that need not be present in other embodiments. For example, the training and evaluation related to that composite model were limited to a single regional health system where most patients are white, so similar models designed and implemented according to the present disclosure may consider a diversity of the relevant patient population and may factor that diversity into the relevant composite model or may adjust the present composite model to account for that diversity. Other models may consider and account for other differences in patient populations, such as physiologic differences across race and/or ethnicity to determine whether these ECG-based models perform differently across groups. In addition, echocardiography-confirmed diagnoses were used to generate the positive labels discussed herein, which were confirmed on chart review to have a high PPV. There may be additional patients with disease—false negatives—who were not captured using this method, although the retrospective deployment discussed herein suggests that the negatives may be overwhelmingly true negatives as compared to false negatives, given the low prevalence of disease. Certain machine-learning approaches may have limited interpretability in identifying feature importance. For example, IVS thickness may represent infiltrative diseases or may represent very poorly controlled hypertension. However, these diseases are important to recognize. Thus, model selection may take interpretability into consideration when identification is desired.

In one aspect of the disclosure, a method comprises: receiving electrocardiogram trace data associated with a patient; receiving clinical data such as an age value and sex value of the patient; providing the electrocardiogram trace data, the age value, and the sex value to a trained composite model, the trained composite model being trained to generate a risk score based on the electrocardiogram trace data, the age value, and the sex value; wherein the risk score reflects the likelihood of a patient having one or more of all of a set of cardiology diseases, the set of cardiology disease comprising aortic stenosis, aortic regurgitation, mitral stenosis, mitral regurgitation, tricuspid regurgitation, abnormal reduced ejection fraction (EF), and abnormal interventricular septal thickness; receiving a risk score indicative of a likelihood the patient will suffer from one of the diseases in the set of cardiology diseases within a predetermined period of time from when the electrocardiogram trace data was generated; and outputting the risk score to at least one of a memory or a display for viewing by a medical practitioner or healthcare administrator. The disclosure also includes an electrocardiogram device containing memory on which are stored computer instructions to perform this method.

The trained composite model may be selected based at least in part on a severity of cardiology diseases the generated risk score represents, and the severity of cardiology diseases may include labels for one or more of normal, mild, moderate, and severe.

The trained composite model may further include a plurality of models, one model for each of the cardiology diseases of the set of cardiology diseases. The plurality of models may generate a respective cardiology disease risk score, and the composite risk score may be based at least in part on one or more of the respective cardiology disease risk scores, where the composite risk score may be a classification based at least in part on a concatenation of the respective cardiology disease risk scores. Additionally or alternatively, the plurality of models may be a plurality of convolutional neural networks.

The predetermined period of time may include times at least one year from when the electrocardiogram trace data was generated.

The trained composite model may include training data associated with a plurality of clinical sites. The trained composite model also may include training the model using patient data associated with one site of the plurality of sites and testing the trained model on the remaining sites of the plurality of sites.

Outputting the composite risk score further comprises outputting the composite risk score to a display of an electrocardiogram monitor and/or to an electronic health records management system.

The method of claim 1, further comprising generating a supplementary risk score for one or more additional cardiology diseases, when the composite risk score exceeds a threshold. The composite risk score may be associated with interventricular septal thickness. Additionally or alternatively, the one or more additional cardiology diseases may include infiltrative diseases, hypertrophic cardiomyopathy, or concentric remodeling.

The clinical data may be selected from demographic data, vitals data, laboratory data, or comorbidities data. Vitals data may include one or more of body mass index, systolic blood pressure, diastolic blood pressure, heart rate, height, weight, or smoking status. Laboratory data may include one or more of A1C, bilirubin, blood urea nitrogen, cholesterol, creatine kinase myocardial band, creatinine, C-reactive protein, D-dimer, glucose, high-density lipoprotein, hemoglobin, high-density lipoprotein, lactate dehydrogenase, lymphocytes, potassium, pro B-type natriuretic peptide, sodium, troponin I and T, triglyceride, uric acid, very low-density lipoprotein, or estimated glomerular filtration rate. Comorbidities data may include one or more of heart failure, prior myocardial infarction, diabetes mellitus, chronic obstructive pulmonary disease, renal failure, prior echocardiogram, coronary artery disease, or hypertension.

The electrocardiogram trace data may include ECG data selected from one or more of acute myocardial infarction, atrial fibrillation, atrial flutter, complete block, early repolarization, fascicular block, first-degree atrioventricular block, intraventricular conduction block, left bundle branch block, right bundle branch block, ischemia, left anterior descending artery ischemia, right bundle branch block, low QRS, left ventricular hypertrophy, non-specific ST-T wave, Non-specific T wave, other bradycardia, premature atrial contractions, pacemaker, poor tracing, prior infarction, prior myocardial infarction anterior, prolonged QT, premature ventricular contractions, right axis deviation, second degree atrioventricular block, sinus bradycardia, supraventricular tachycardia, tachycardia, tachyarrhythmia, T inversion, or ventricular tachycardia at a time when the electrocardiogram data was generated.

The method also may include the step of providing measurements from echocardiogram data to the trained composite model, and the measurements from echocardiogram data may include measurements selected from one or more of average R-R interval, P-R interval, P axis, QRS duration, QT, QTC, R axis, T axis, or ventricular rate.

The method also may include gathering the clinical data and electrocardiogram trace data based at least in part on a presence of ICD codes associated with the patient. The electrocardiogram trace data may include at least 8 leads and may be sampled at 250 hz or 500 hz.

Training the trained composite model may include receiving training data associated with a plurality of patients, each of the patients having received an echocardiogram; generating a patient timeline for each patient of the plurality of patients; anchoring each respective patient timeline to a date of occurrence of an echocardiogram; and labeling each respective patient as having a positive or negative ECG based at least in part on the date of an ECG with respect to the date of occurrence of the echocardiogram. The method further may include excluding patients from training after a censoring event is detected in the patient timeline.

When the composite risk score exceeds a predetermined threshold, the method also may include generating a notification to provide additional monitoring of the patient, the additional monitoring including an echocardiogram.

In another aspect of the disclosure, a method comprises: receiving electrocardiogram trace data associated with a plurality of patients comprising at least 100 patients; receiving an age value and sex value of each patient in the plurality of patients; providing the electrocardiogram trace data, the age value, and the sex value of each patient in the plurality of patients to a trained composite model, the trained composite model being trained to generate a risk score for each corresponding patient based on the electrocardiogram trace data, the age value, and the sex value; wherein the risk score reflects the likelihood of the corresponding patient having one or more of all of a set of cardiology diseases, the set of cardiology disease comprising aortic stenosis, aortic regurgitation, mitral stenosis, mitral regurgitation, tricuspid regurgitation, abnormal reduced ejection fraction (EF), and abnormal interventricular septal thickness; receiving a corresponding risk score indicative of a likelihood the corresponding patient will suffer from one of the diseases in the set of cardiology diseases within a predetermined period of time from when the electrocardiogram trace data was generated; and outputting the corresponding risk score to at least one of a memory or a display for viewing by a medical practitioner or healthcare administrator.

In addition to the cardiac diseases discussed above (aortic stenosis [AS], aortic regurgitation [AR], mitral stenosis [MS], mitral regurgitation [MR], tricuspid regurgitation [TR], reduced left ventricular ejection fraction [EF], and increased interventricular septal [IVS] thickness), the composite model disclosed herein may be used or modified to predict additional cardiac disease states. In one aspect, this may involve modifying the training inputs and/or input data to include inputs determined to be relevant to those disease states. In another aspect, however, the same training inputs and/or input data used to develop and/or implement the composite model discussed above also may be used to identify patients likely to experience the other cardiac disease state(s). In particular, the model may be used to identify patients likely to experience hypertrophic cardiomyopathy [HCM] since components of the present model, or one or more of the other disease states related to that model, such as mitral regurgitation and increased IVS (for example, greater than 15 mm), may also be associated with HCM. Thus, the present composite model may be used to identify patients likely to experience HCM without needing to train the model specifically on HCM.

In order to compare results generated by a model such as the one disclosed herein and then applied to HCM vs an HCM-specific model, a first, composite model was generated using the techniques discussed herein with regard to a de-identified dataset of 2,898,979 ECGs acquired from 661,366 unique patients between 1984-2021, the dataset linked to electronic health records and echocardiograms when available. From this dataset, the composite model was trained on 1,869,436 ECGs with a composite structural heart disease label. Separately, a second, HCM-specific model was also trained on 2,022,942 ECGs with a binary HCM label.

To enable comparison between the two models, both models were tested on a shared heldout set (ECG prevalence: 1.24%, patient prevalence: 0.52%). When the heldout set was applied to both models, it was determined that the first model exhibited comparable performance to the second, HCM-specific model. In particular, despite it being trained to identify the first model, the AUROC for the second model was 90 [95% CI: 89,91] while the AUROC for the first model was 92 [95% CI: 90,93]. Moreover, at an operating point optimized for an F1-score, the sensitivity to HCM was higher for the first model at 42 [95% CI: 33,50] than for the second model at 18 [95% CI: 15,21].

Figure 6:
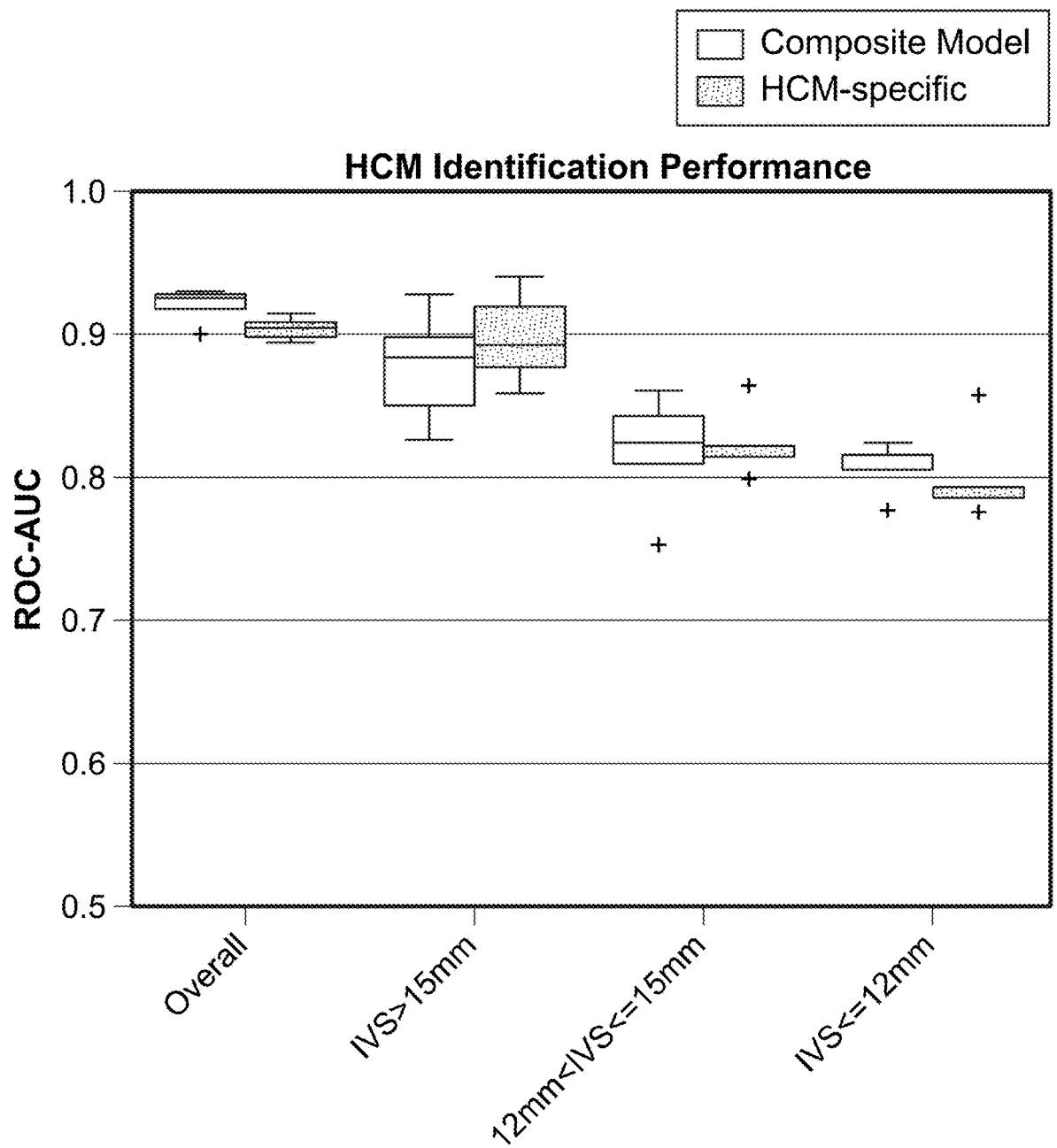
FIG. 6 is a graph depicting performance of the composite model versus a model specifically trained to identify hypertrophic cardiomyopathy for a range of IVS thicknesses.

Moreover, as seen in FIG. 6, the first, composite model sustained its performance across a range of IVS thicknesses, despite only being trained to identify IVS>15 mm.

Figure 7A:
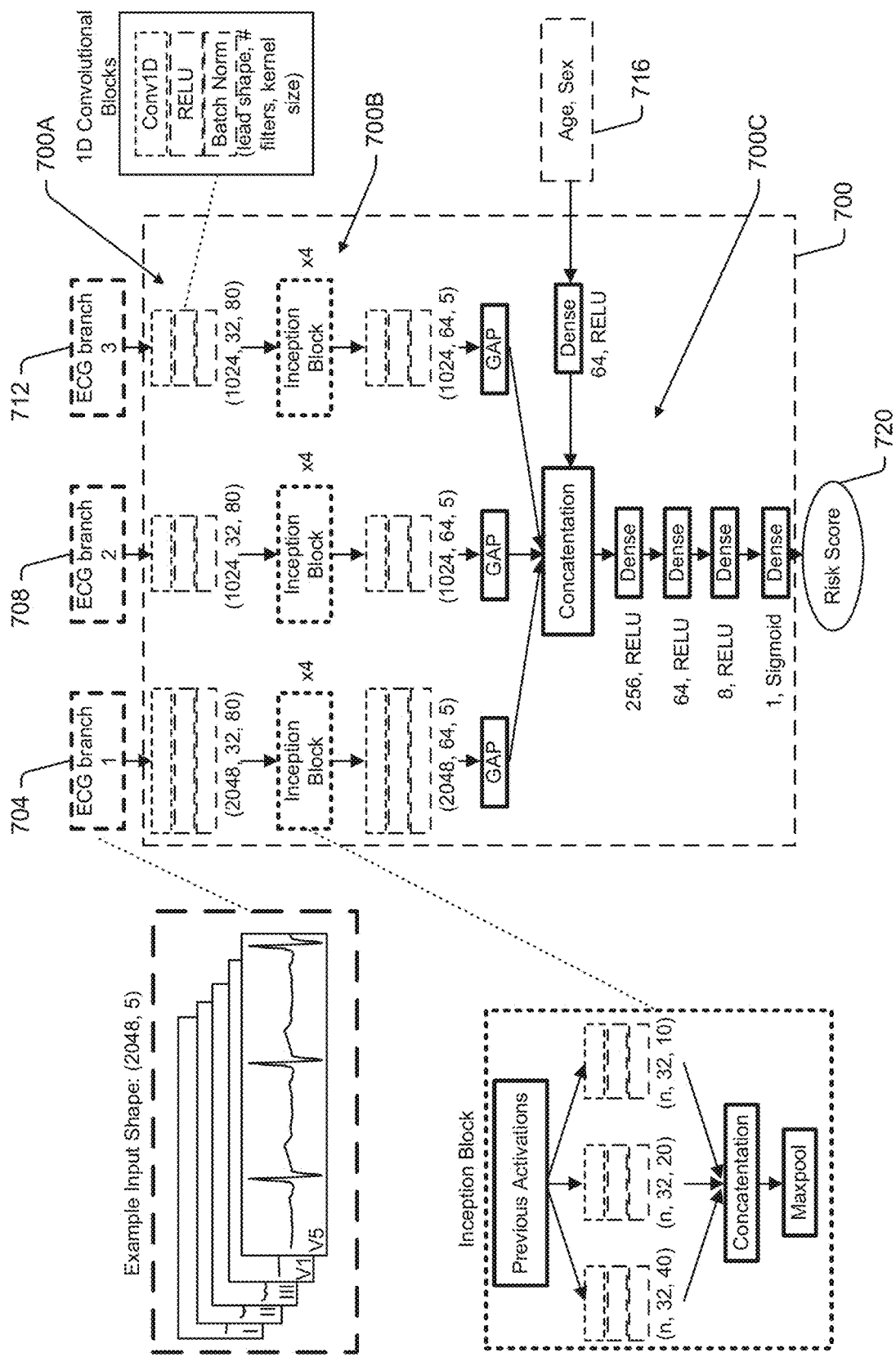
FIG. 7A is an exemplary embodiment of a model.

FIG. 7A is an exemplary embodiment of a model 600. Specifically, an architecture of the model 600 is shown. Artificial intelligence models referenced herein, including model 700 and model 724 discussed further below, may be gradient boosting models, random forest models, neural networks (NN), regression models, Naïve Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short-term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

Figure 5:
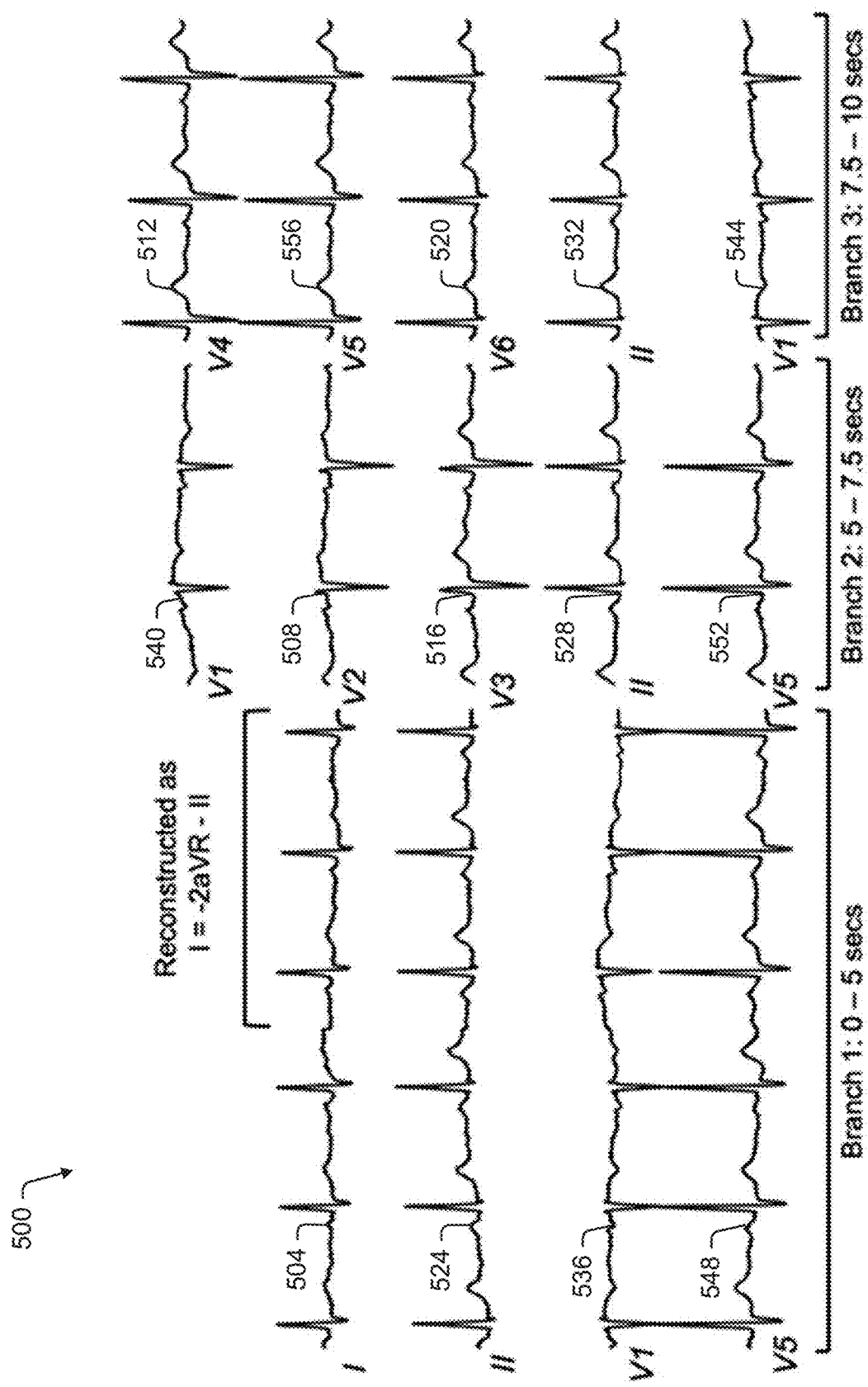
FIG. 5 is an example of raw ECG voltage input data.

In some embodiments, the model 700 can be a deep neural network. In some embodiments, the model 700 can receive the input data shown in FIG. 5. The input data structure to the model 700 can include a first branch 704 including leads I, II, V1, and V5, acquired from time (t)=0 (start of data acquisition) to t=5 seconds (e.g., the first voltage data, the sixth voltage data, the ninth voltage data, and the twelfth voltage data); a second branch 708 including leads V1, V2, V3, II, and V5 from t=5 to t=7.5 seconds (e.g., the second voltage data, the fourth voltage data, the seventh voltage data, the tenth voltage data, and the thirteenth voltage data); and a third branch 712 including leads V4, V5, V6, II, and V1 from t=7.5 to t=10 seconds (e.g., the third voltage data, the fifth voltage data, the eighth voltage data, the eleventh voltage data, and the fourteenth voltage data) as shown in FIG. 5. The arrangement of the branches can be designed to account for concurrent morphology changes throughout the standard clinical acquisition due to arrhythmias and/or premature beats. For example, the model 700 may need to synchronize which voltage information or data is acquired at the same point in time in order to understand the data. Because the ECG leads are not all acquired at the same time, the leads may be aligned to demonstrate to the neural network model which data was collected at the same time. It is noted that not every lead needs to have voltage data spanning the entire time interval. This is an advantage of the model 700, as some ECGs do not include data for all leads over the entire time interval. For example, the model 700 can include ten branches, and can be trained to generate a risk score based in response to receiving voltage data spanning subsequent one second periods from ten different leads. As another example, the model 700 can include four branches, and can be trained to generate a risk score based in response to receiving voltage data spanning subsequent 2.5 second periods from four different leads. Certain organizations such as hospitals may use a standardized ECG configuration (e.g., voltage data spanning subsequent one second periods from ten different leads). The model 700 can include an appropriate number of branches and be trained to generate a risk score for the standardized ECG configuration. Thus, the model 700 can be tailored to whatever ECG configuration is used by a given organization.

In some embodiments, the model 700 can include a convolutional component 700A, inception blocks 700B, and a fully connected dense layer component 700C. The convolutional component 700A may start with an input for each branch followed by a convolutional block. Each convolutional block included in the convolutional component 700A can include a 1D convolutional layer, a rectified linear activation (RELU) activation function, and a batchnorm layer, in series. Next, this convolutional block can be followed by four inception blocks 700B in series, where each inception block 700B may include three 1D convolutional blocks concatenated across the channel axis with decreasing filter window sizes. Each of the four inception blocks 700B can be connected to a 1D max pooling layer, where they are connected to another single 1D convolutional block and a final global averaging pool layer. The outputs for all three branches can be concatenated and fully connected to the dense layer component 700C. The dense layer component 700C can include four dense layers of 256, 64, 8 and 1 unit(s) with a sigmoid function as the final layer. All layers in the architecture can enforce kernel constraints and may not include bias terms. In some embodiments, an AdaGrad optimizer can be used with a learning rate of $1e^{-4}$ 45, a linear learning rate decay of 1/10 prior to early stopping for efficient model convergence, and batch size of 2048. While AdaGrad is presented, other examples of algorithms which adaptively update the learning rate of a model, such as through stochastic gradient descent iterative methods include RMSProp, Adam, and backpropagation learning such as the momentum method. In some embodiments, the model 700 can be implemented using one or more machine learning libraries, such as Keras, PyTorch, TernsorFlow, Theano, MXNet, scikit-learn, CUDA, Kubeflow, or MLflow. For example, the model 700 may be implemented using Keras with a TensorFlow backend in python, and default training parameters were used except where specified. In some embodiments, AdaGrad optimizer can be used with a learning rate of $1e^{-4}$ $^{45}$, a linear learning rate decay of 1/10 prior to early stopping for efficient model convergence at patience of three epochs, and batch size of 2048. In some embodiments, differing model frameworks, hypertuning parameters, and/or programming languages may be implemented. The patience for early stopping was set to 9 epochs. In some embodiments, the model 700 can be trained using NVIDIA DGX1 and DGX2 machines with eight and sixteen V100 GPUs and 32 GB of RAM per GPU, respectively.

In some embodiments, the model 700 can additionally receive electronic health record (EHR) data points such as demographic data 716, which can include age and sex/gender as input features to the network, where sex can be encoded into binary values for both male and female, and age can be cast as a continuous numerical value corresponding to the date of acquisition for each 12-lead resting state ECG. In some embodiments, other representations may be used, such as an age grouping 0-9 years, 10-19 years, 20-29 years, or other grouping sizes. In some embodiments, other demographic data such as race, smoking status, height, and/or weight may be included. In some embodiments, the EHR data points can include laboratory values, echo measurements, ICD codes, and/or care gaps. The EHR data points (e.g., demographic data, laboratory values, etc.) can be provided to the model 700 at a common location.

The EHR data points (e.g., age and sex) can be fed into a 64-unit hidden layer and concatenated with the other branches. In some instances, these EHR features can be extracted directly from the standard 12-lead ECG report. In some embodiments, the model 700 can generate ECG information based on voltage data from the first branch 704, the second branch 708, and the third branch 712. In some embodiments, the model 700 can generate demographic information based on the demographic data 716. In some embodiments, the demographic information can be generated by inputting age and sex were input into a 64-unit hidden layer. The demographic information can be concatenated with the ECG information, and the model 700 can generate a risk score 720 based on the demographic information and the ECG information. Concatenating the ECG information with the separately generated demographic information can allow the model 700 to individually disseminate the voltage data from the first branch 704, the second branch 708, and the third branch 712, as well as the demographic data 716, which may improve performance over other models that provide the voltage data and the demographic data 716 to the model at the same channel.

In some embodiments, the model 700 can be included in the trained models 936 of FIG. 9, discussed below. In some embodiments, the risk score 720 can be indicative of a likelihood the patient will suffer from one or more conditions within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. For example, in some embodiments, the model 700 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years.

Figure 7B:
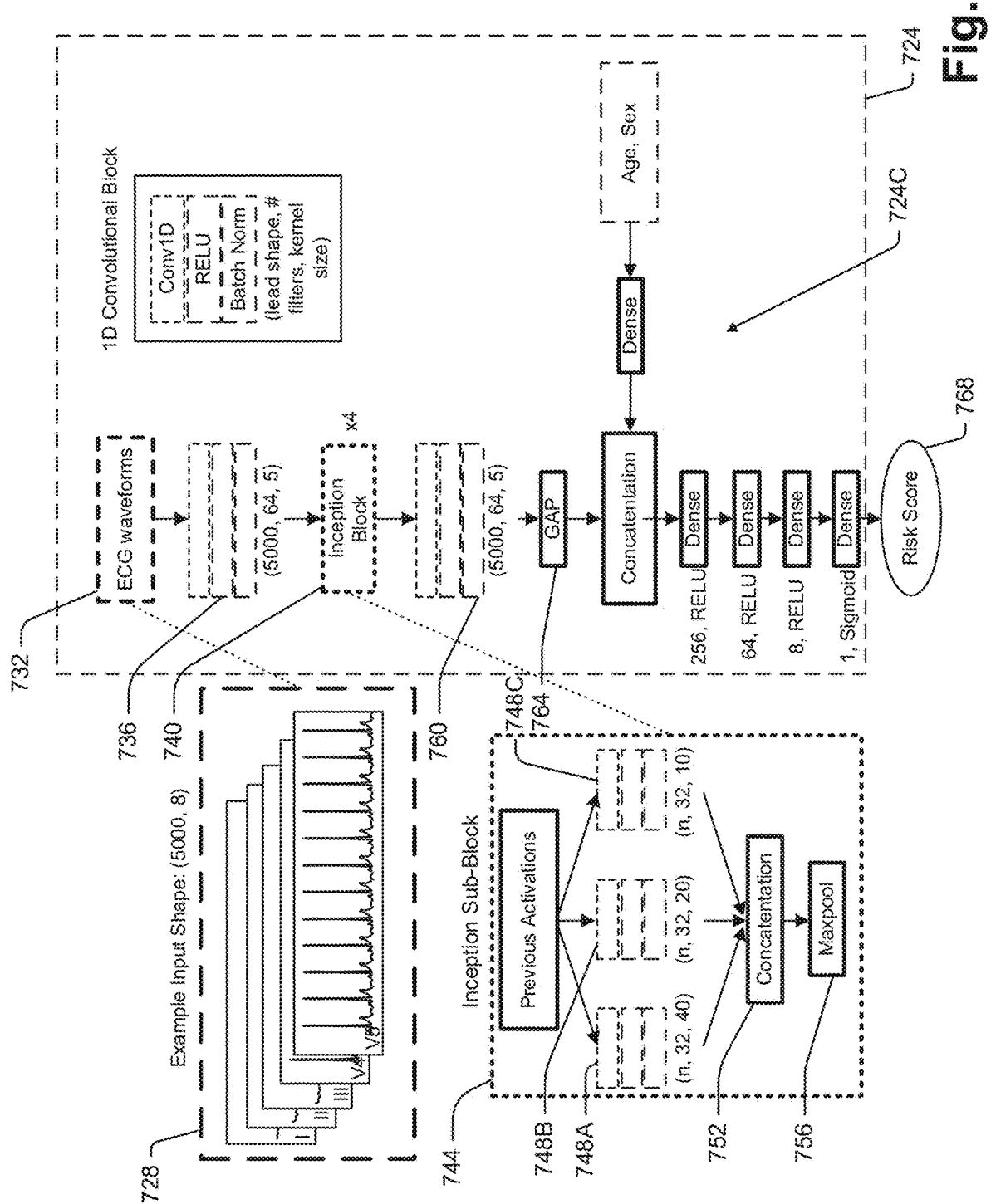
FIG. 7B is another exemplary embodiment of a model.

FIG. 7B is another exemplary embodiment of a model 724. Specifically, another architecture of the model 700 in FIG. 7A is shown. In some embodiments, the model 724 in FIG. 7B can receive ECG voltage data generated over a single time interval.

In some embodiments, the model 724 can be a deep neural network. In some embodiments, such as is shown in FIG. 7B, the model 724 can include a single branch 732 that can receive ECG voltage input data 728 generated over a single time interval (e.g., ten seconds). As shown, the model 724 can receive ECG voltage input data 728 generated over a time interval of ten seconds using eight leads. In some embodiments, the ECG voltage input data 728 can include five thousand data points collected over a period of 10 seconds and 8 leads including leads I, II, V1, V2, V3, V4, V5, and V6. The number of data points can vary based on the sampling rate used to sample the leads (e.g., a sampling rate of five hundred Hz will result in five thousand data points over a time period of ten seconds). The ECG voltage input data 728 can be transformed into ECG waveforms.

As described above, in some embodiments, the ECG voltage input data 728 can be "complete" and contain voltage data from each lead (e.g., lead I, lead V2, lead V4, lead V3, lead V6, lead II, lead VI, and lead V5) generated over the entire time interval. Thus, in some embodiments, the predetermined ECG configuration can include lead I, lead V2, lead V4, lead V3, lead V6, lead II, lead VI, and lead V5 having time intervals of 0-10 seconds. The model 724 can be trained using training data having the predetermined ECG configuration including lead I, lead V2, lead V4, lead V3, lead V6, lead II, lead VI, and lead V5 having time intervals of 0-10 seconds. When all leads share the same time intervals, the model can receive the ECG voltage input data 728 at a single input branch 732. Otherwise, the model can include a branch for each unique time interval may be used as described above in conjunction with FIG. 7A.

The ECG waveform data for each ECG lead may be provided to a 1D convolutional block 736 where the layer definition parameters (n, f, s) refer, respectively, to the number of data points input presented to the block, the number of filters used, and the filter size/window. In some embodiments, the number of data points input presented to the block can be five thousand, the number of filters used can be thirty-two, and the filter size/window can be eighty. The 1D convolutional block 736 can generate and output a downsampled version of the inputted ECG waveform data to the inception block. In some embodiments, the first 1D convolutional block 736 can have a stride value of two.

The model 724 can include an inception block 740. In some embodiments, the inception block 740 can include a number of sub-blocks. Each sub-block 744 can include a number of convolutional blocks. For example, each sub-block 744 can include a first convolutional block 748A, a second convolutional block 748B, and a third convolutional block 748C. In the example shown in FIG. 7B, the inception block 740 can include four sub-blocks in series, such that the output of each sub-block is the input to the next sub-block. Each inception sub-block can generate and output a downsampled set of time-series information. Each sub-block can be configured with filters and filter windows as shown in the inception block 740 with associated layer definition parameters.

In some embodiments, the first convolutional block 748A, the second convolutional block 748B, and the third convolutional block 748C can be 1D convolutional blocks. Results from each of the convolutional blocks 744A-C can be concatenated 752 by combining the results (e.g., arrays), and inputting the concatenated results to a downsampling layer, such as a MaxPool layer 756 included in the sub-block 744. The MaxPool layer 756 can extract positive values for each moving 1D convolutional filter window, and allows for another form of regularization, model generalization, and prevent overfitting. After completion of all four inception block processes, the output is passed to a final convolutional block 760 and then a global average pooling (GAP) layer 764. The purpose of the GAP layer 764 is to average the final downsampled ECG features from all eight independent ECG leads into a single downsampled array. The output of the GAP layer 764 can be passed into the series of dense layer components 724C as in conjunction with FIG. 7A (e.g., at the dense layer component 700C). Furthermore, optimization parameters can also be set for all layers. For example, all layer parameters can enforce a kernel constraint parameter (max_norm=3), to prevent overfitting the model. The first convolutional block 736 and the final convolutional block 760 can utilize a stride parameter of n=1, whereas each inception block 740 can utilize a stride parameter of n=2. The stride parameters determine the movement of every convolutional layer across the ECG time series and can have an impact on model performance. In some embodiments, the model 724 can also concatenate supplementary data such as age and sex as described above in conjunction with FIG. 7A, and the model 724 can utilize the same dense layer component architecture as the model 700. The model 724 can output a risk score 768 based on the demographic information and the ECG information. Specifically, the dense layer components 724C can output the risk score 768. In some embodiments, the risk score 720 can be indicative of a likelihood the patient will suffer from a condition within a predetermined period of time from when electrocardiogram data (e.g., the voltage data from the leads) was generated. In some embodiments, the condition can be AF, mortality, ST-Elevation Myocardial Infarction (STEMI), Acute coronary syndrome (ACS), stroke, or other conditions indicated herein. In some embodiments, for example, the model 700 can be trained to predict the risk of a patient developing AF in a predetermined time period following the acquisition of an ECG based on the ECG. In some embodiments, the time period can range from one day to thirty years. For example, the time period may be one day, three months, six months, one year, five years, ten years, and/or thirty years.

Figure 8A:
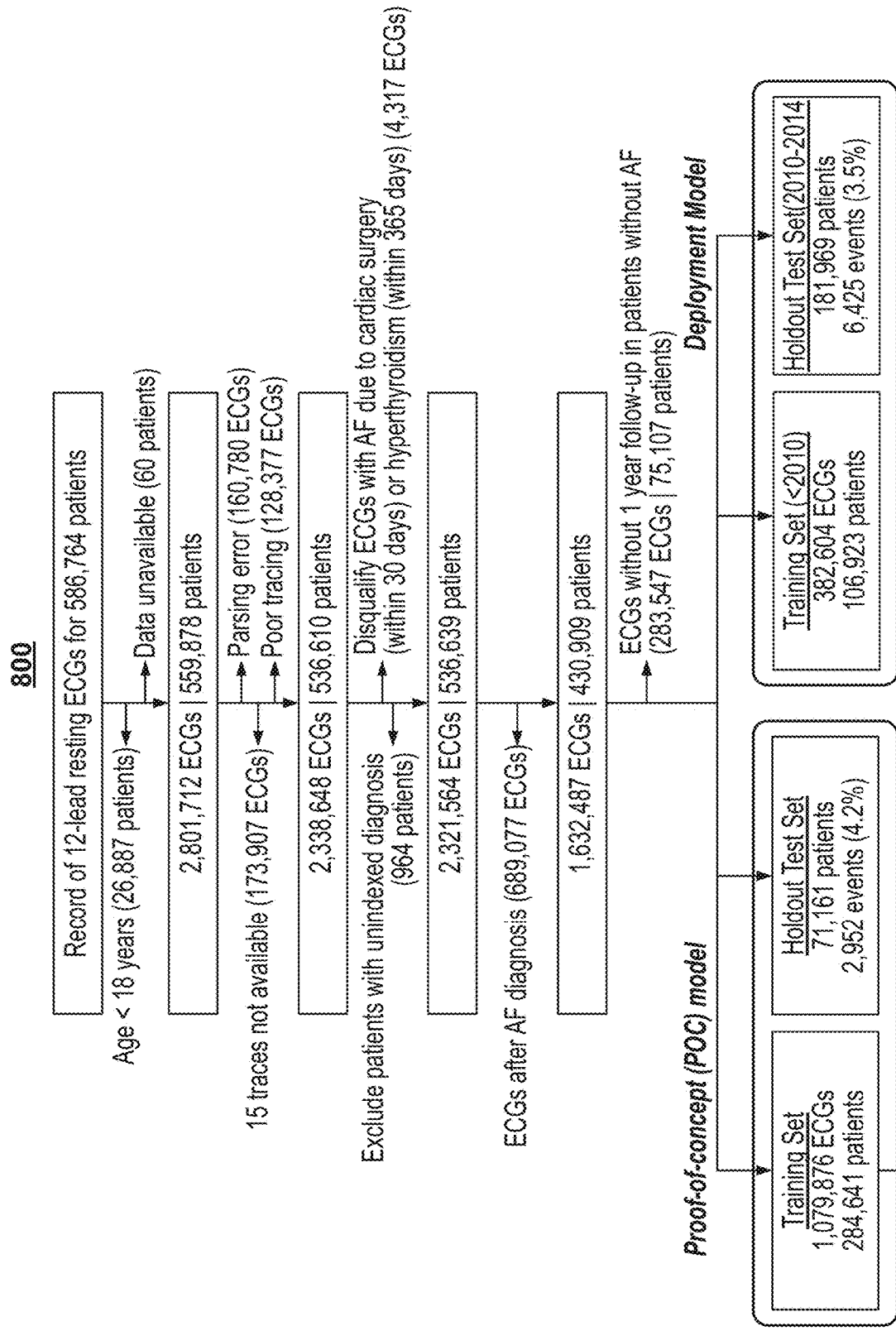
FIG. 8A is an exemplary flow of training and testing the model of FIG. 6A.
Figure 8B:
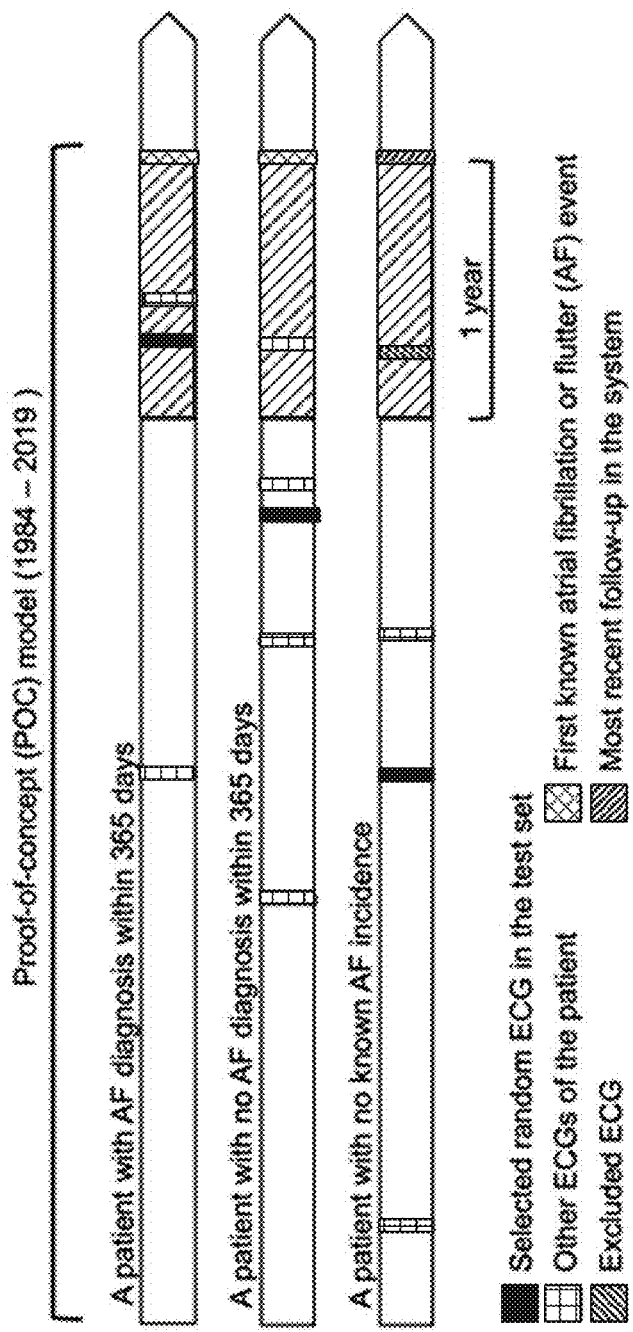
FIG. 8B shows a timeline for ECG selection in accordance with FIG. 7A.

FIG. 8A is an exemplary flow 800 of training and testing the model 800 in FIG. 8A, although it will be appreciated that other training and/or testing procedures may be implemented. 2.8 million standard 12-lead ECG traces were extracted from a medical database. All ECGs with known time-to-event or minimum 1-year follow-up were used during model training and a single random ECG was selected for each patient in the holdout set for model evaluation, with results denoted as 'MO' in FIG. 8B. FIG. 8B shows a timeline for ECG selection in accordance with FIG. 8A. The traces were acquired between 1984 and June 2019. Additional retraining was performed only the resting 12-lead ECGs: 1) acquired in patients ≥18 years of age, 2) with complete voltage-time traces of 2.5 seconds for 12 leads and 10 seconds for 3 leads (V1, II, V5), and 3) with no significant artifacts. This amounted to 1.6 million ECGs from 431k patients. The median (interquartile range) follow-up available after each ECG was 4.1 (1.5-8.5) years. Each ECG was defined as normal or abnormal as follows: 1) normal ECGs were defined as those with pattern labels of "normal ECG" or "within normal limits" and no other abnormalities identified; 2) all other ECGs were considered abnormal. Note that a normal ECG does not imply that the patient was free of heart disease or other medical diagnoses. All the ECG voltage-time traces were preprocessed to ensure that waveforms were centered around the zero baseline, while preserving variance and magnitude features.

All studies from patients with pre-existing or concurrent documentation of AF were excluded, it being understood that this process can be adapted to patients with pre-existing or concurrent documentation of one or more other disease types if the model 700 is being used to evaluate ECG data with respect to those disease types in addition to or instead of AF. Thus, it should be understood that the discussion below can be adapted to those other disease states by substituting those disease states for the "AF" references and/or by defining features of those disease states. The AF phenotype was defined as a clinically reported finding of atrial fibrillation or atrial flutter from a 12-lead ECG or a diagnosis of atrial fibrillation or atrial flutter applied to two or more inpatient or outpatient encounters or on the patient problem list from the institutional electronic health record (EHR) over a 24-year time period. Any new diagnoses occurring within 30 days following cardiac surgery or within one year of a diagnosis of hyperthyroidism were excluded. Details on the applicable diagnostic codes and blinded chart review validation of the AF phenotype are provided in Table 14 below. Atrial flutter was grouped with atrial fibrillation because the clinical consequences of the two rhythms are similar, including the risk of embolization and stroke, and because the two rhythms often coexist. In some embodiments, differing data may be selected for training, validation, and/or test sets of the model.

Table 14 shows performance measures for the blinded chart review of the AF phenotype definition. Diagnostic codes (ICD 9, 10 and EDG) and corresponding description may be used in defining AF phenotype.

TABLE 14

| Blinded chart review validation (AF phenotype) | |
| --- | --- |
| Positive Predictive Value | 94.4% |
| Negative Predictive Value | 100% |
| Sensitivity | 100% |
| Specificity | 91.6% |
| True Positive | 117 |
| True Negative | 76 |
| False Positive | 7 |
| False Negative | 0 |

AF was considered "new onset" if it occurred at least one day after the baseline ECG at which time the patient had no history of current or prior AF. EHR data were used to identify the most recent qualifying encounter date for censorship. Qualifying encounters were restricted to ECG, echocardiography, outpatient visit with internal medicine, family medicine or cardiology, any inpatient encounter, or any surgical procedure.

For all experiments, data were divided into training, internal validation, and test sets. The composition of the training and test sets varied by experiment, as described below; however, the internal validation set in all cases was defined as a 20% subset of the training data to track validation area under the receiver operating characteristic curve (AUROC) during training to avoid overfitting by early stopping. The patience for early stopping was set to 9 and the learning rate was set to decay after 3 epochs when there was no improvement in the AUROC of the internal validation set during training.

The models were evaluated using the AUROC, which is a robust metric of model performance that represents the ability to discriminate between two classes. Higher AUROC suggests higher performance (with perfect discrimination represented by an AUROC of 1 and an AUROC of 0.5 being equivalent to a random guess). Multiple AUROCs were compared by bootstrapping 1000 instances (using random and variable sampling with replacement). Differences between models were considered statistically significant if the absolute difference in the 95% CI was greater than zero. The models were also evaluated using area under the precision recall curve (AUPRC) as average precision score by computing weighted average of precisions achieved at each threshold by the increase in recall.

Figure 9:
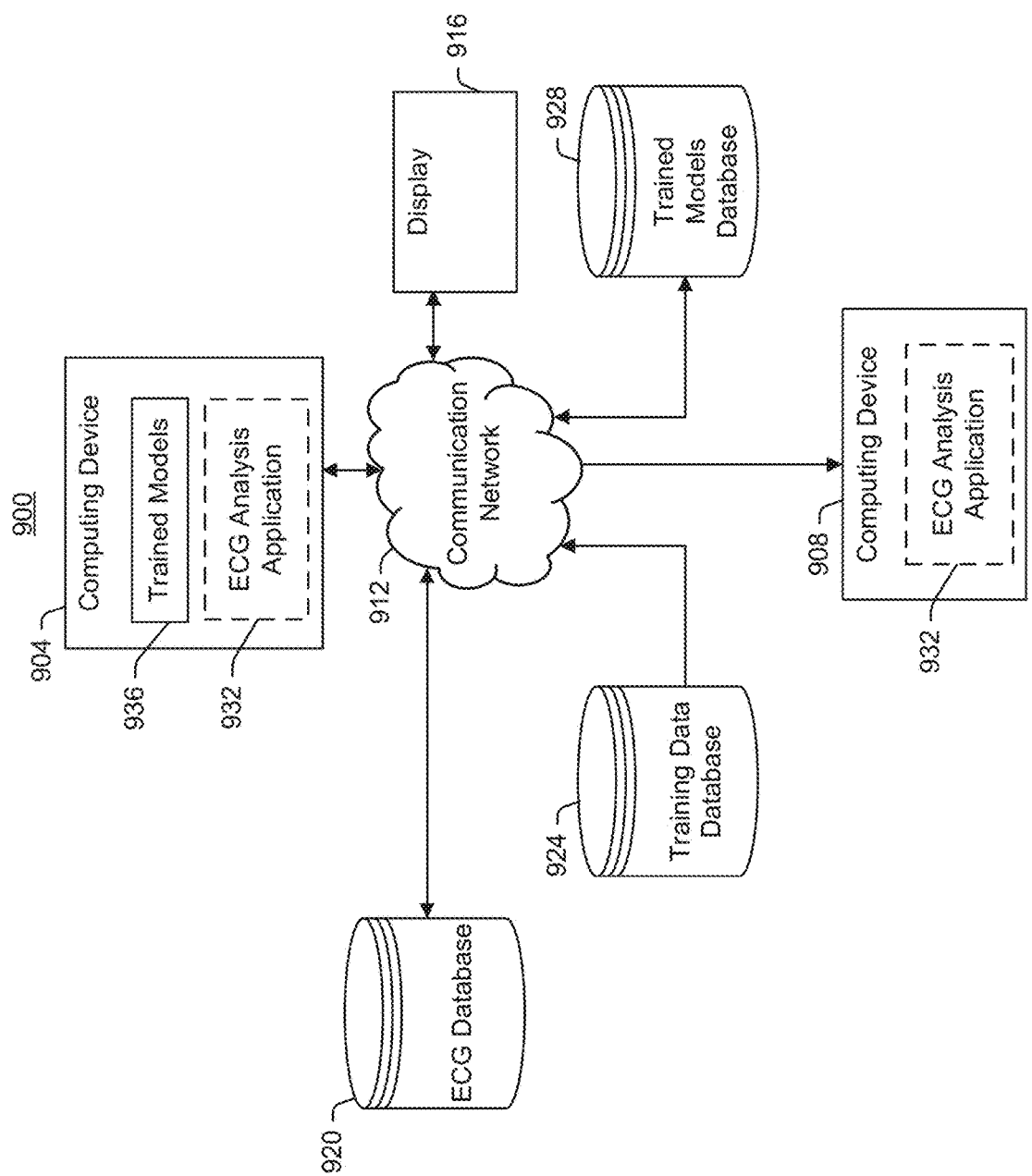
FIG. 9 is an example of a system for automatically predicting an Atrial fibrillation (AF) risk score based on electrocardiogram (ECG) data.

FIG. 9 is an example 900 of a system 900 for automatically predicting a cardiac disease state risk score based on ECG data (e.g., data from a resting 12-lead ECG). In some embodiments, the system 900 can include a computing device 904, a secondary computing device 908, and/or a display 916. In some embodiments, the system 900 can include an ECG database 920, a training data database 924, and/or a trained models database 928. In some embodiments, the computing device 904 can be in communication with the secondary computing device 908, the display 916, the ECG database 920, the training data database 924, and/or the trained models database 928 over a communication network 912. As shown in FIG. 9, the computing device 904 can receive ECG data, such as 12-lead ECG data, and generate a cardiac disease state risk score based on the ECG data. In some embodiments, the risk score can indicate a predicted risk of a patient developing the cardiac event within a predetermined time period from when the ECG was taken (e.g., three months, six months, one year, five years, ten years, etc.). In some embodiments, the computing device 904 can execute at least a portion of an ECG analysis application 932 to automatically generate the cardiac disease state risk score.

The system 900 may generate a risk score to provide physicians with a recommendation to consider additional cardiac monitoring for patients who are most likely to experience atrial fibrillation, atrial flutter, or another relevant condition within the predetermined time period. In some examples, the system 900 may be indicated for use in patients aged 40 and older without current AF or prior AF history. In some examples, the system 900 may be indicated for use in patients without pre-existing and/or concurrent documentation of AF or other relevant condition. In some examples, the system 900 may be used by healthcare providers in combination with a patient's medical history and clinical evaluation to inform clinical decision making.

In some embodiments, the ECG data may be indicative or not indicative of a heart condition based on cardiological standards. For example, the ECG data may be indicative of a fast heartbeat. The system 900 may predict a risk score indicative that the patient will suffer from the cardiac condition (e.g., AF) based on ECG data that is not indicative of a given heart condition (e.g., fast heartbeat). In this way, the system may detect patients at risk for one or more conditions even when the ECG data appears "healthy" based on cardiological standards. The system 900 may predict a risk score indicative that the patient will suffer from the condition (e.g., AF) based on ECG data that is indicative of a heart condition (e.g., fast heartbeat). In this way, the system 900 may detect patients at risk for one or more conditions when the ECG data indicates the presence of a different condition.

The ECG analysis application 932 can be included in the secondary computing device 908 that can be included in the system 900 and/or on the computing device 904. The computing device 904 can be in communication with the secondary computing device 908. The computing device 904 and/or the secondary computing device 908 may also be in communication with a display 916 that can be included in the system 900 over the communication network 912. In some embodiments, the computing device 904 and/or the secondary computing device 908 can cause the display 916 to present one or more AF risk scores and/or reports generated by the ECG analysis application 932.

The communication network 912 can facilitate communication between the computing device 904 and the secondary computing device 908. In some embodiments, the communication network 912 can be any suitable communication network or combination of communication networks. For example, the communication network 912 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, the communication network 912 can be a local area network, a wide area network, a public network (e.g., the Internet), a private or semi-private network (e.g., a corporate or university intranet), any other suitable type of network, or any suitable combination of networks. Communications links shown in FIG. 9 can each be any suitable communications link or combination of communications links, such as wired links, fiber optic links, Wi-Fi links, Bluetooth links, cellular links, etc.

The ECG database 920 can include a number of ECGs. In some embodiments, the ECGs can include 12-lead ECGs. Each ECG can include a number of voltage measurements taken at regular intervals (e.g., at a rate of 250 HZ, 500 Hz, 1000 Hz, etc.) over a predetermined time period (e.g., 5 seconds, 10 seconds, 15 seconds, 30 seconds, 60 seconds, etc.) for each lead. In some instances, the number of leads may vary (e.g., from 1-12) and the respective sampling rates and time periods may be different for each lead. In some embodiments, the ECG can include a single lead. In some embodiments, the ECG database 920 can include one or more AF risk scores generated by the ECG analysis application 932.

The training data database 924 can include a number of ECGs and clinical data. In some embodiments, the clinical data can include outcome data, such as whether or not a patient developed AF in a time period following the day that the ECG was taken. Exemplary time periods may include 1 month, 2 months, 3 months, 4 months, 5 months, 6 months, 7 months, 8 months, 9 months, 10 months, 11 months 12 months, 1 year, 2 years, 3 years, 4 years, 5 years, 6 years, 7 years, 8 years, 9 years, or 10 years. The ECGs and clinical data can be used for training a model to generate AF risk scores. In some embodiments, the training data database 924 can include multi-lead ECGs taken over a period of time (such as ten seconds) and corresponding clinical data. In some embodiments, the trained model's database 928 can include a number of trained models that can receive raw ECGs and output AF risk scores. In other embodiments, a digital image of a lead for an ECG may be used. In some embodiments, trained models 936 can be stored in the computing device 904.

Figure 10:
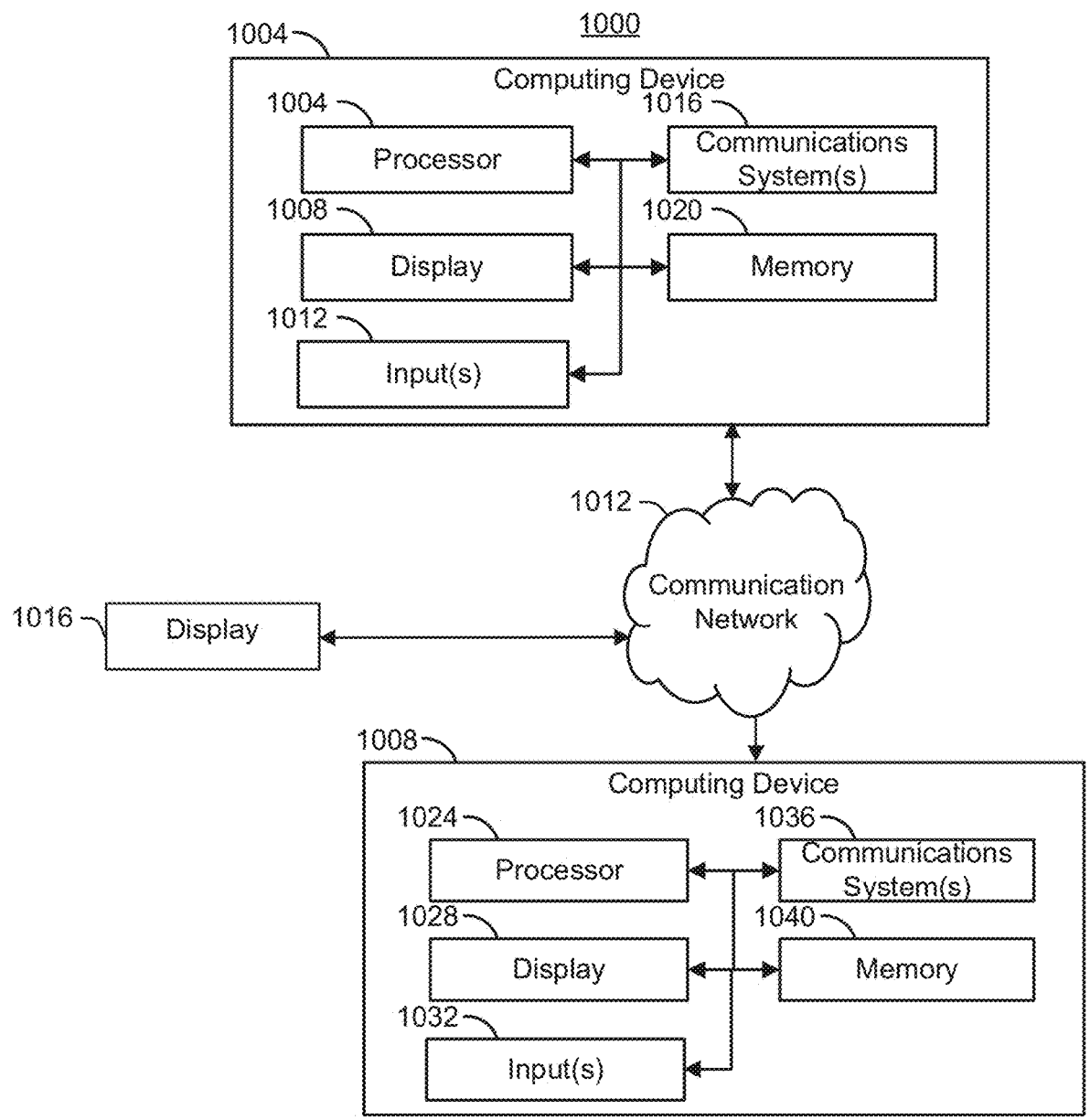
FIG. 10 is an example of hardware that can be used in some embodiments of the system of FIG. 9.

FIG. 10 is an example of hardware that can be used in some embodiments of the system 900. The computing device 904 can include a processor 1004, a display 1008, one or more input(s) 10912, one or more communication system(s) 1016, and a memory 1020. The processor 1004 can be any suitable hardware processor or combination of processors, such as a central processing unit ("CPU"), a graphics processing unit ("GPU"), etc., which can execute a program, which can include the processes described below.

In some embodiments, the display 1008 can present a graphical user interface. In some embodiments, the display 1008 can be implemented using any suitable display devices, such as a computer monitor, a touchscreen, a television, etc. In some embodiments, the input(s) 1012 of the computing device 904 can include indicators, sensors, actuatable buttons, a keyboard, a mouse, a graphical user interface, a touch-screen display, etc.

In some embodiments, the communication system(s) 1016 can include any suitable hardware, firmware, and/or software for communicating with the other systems, over any suitable communication networks. For example, the communication system 1016 can include one or more transceivers, one or more communication chips and/or chip sets, etc. In a more particular example, communication system 1016 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 1016 allows the computing device 904 to communicate with the secondary computing device 908.

In some embodiments, the memory 1020 can include any suitable storage device or devices that can be used to store instructions, values, etc., that can be used, for example, by the processor 1004 to present content using display 1008, to communicate with the secondary computing device 908 via communications system(s) 1016, etc. The memory 1020 can include any suitable volatile memory, non-volatile memory, storage, or any suitable combination thereof. For example, the memory 1020 can include RAM, ROM, EEPROM, one or more flash drives, one or more hard disks, one or more solid state drives, one or more optical drives, etc. In some embodiments, the memory 1020 can have encoded thereon a computer program for controlling operation of computing device 904 (or secondary computing device 908). In such embodiments, the processor 904 can execute at least a portion of the computer program to present content (e.g., user interfaces, images, graphics, tables, reports, etc.), receive content from the secondary computing device 908, transmit information to the secondary computing device 908, etc.

The secondary computing device 908 can include a processor 1024, a display 1028, one or more input(s) 1032, one or more communication system(s) 1036, and a memory 1040. The processor 1024 can be any suitable hardware processor or combination of processors, such as a central processing unit ("CPU"), a graphics processing unit ("GPU"), etc., which can execute a program, which can include the processes described below.

In some embodiments, the display 1028 can present a graphical user interface. In some embodiments, the display 1028 can be implemented using any suitable display devices, such as a computer monitor, a touchscreen, a television, etc. In some embodiments, the inputs 1032 of the secondary computing device 908 can include indicators, sensors, actuatable buttons, a keyboard, a mouse, a graphical user interface, a touch-screen display, etc.

In some embodiments, the communication system(s) 1036 can include any suitable hardware, firmware, and/or software for communicating with the other systems, over any suitable communication networks. For example, the communication system 1036 can include one or more transceivers, one or more communication chips and/or chip sets, etc. In a more particular example, communication system(s) 1036 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system(s) 1036 allows the secondary computing device 908 to communicate with the computing device 904.

In some embodiments, the memory 1040 can include any suitable storage device or devices that can be used to store instructions, values, etc., that can be used, for example, by the processor 1024 to present content using display 1028, to communicate with the computing device 904 via communications system(s) 1036, etc. The memory 1040 can include any suitable volatile memory, non-volatile memory, storage, or any suitable combination thereof. For example, the memory 1040 can include RAM, ROM, EEPROM, one or more flash drives, one or more hard disks, one or more solid state drives, one or more optical drives, etc. In some embodiments, the memory 1040 can have encoded thereon a computer program for controlling operation of secondary computing device 908 (or computing device 904). In such embodiments, the processor 1024 can execute at least a portion of the computer program to present content (e.g., user interfaces, images, graphics, tables, reports, etc.), receive content from the computing device 904, transmit information to the computing device 904, etc.

The display 916 can be a computer display, a television monitor, a projector, or other suitable displays.

While the invention may be susceptible to various modifications and alternative forms, specific embodiments have been shown by way of example in the drawings and have been described in detail herein. However, it should be understood that the invention is not intended to be limited to the particular forms disclosed.

Thus, the invention is to cover all modifications, equivalents, and alternatives falling within the spirit and scope of the invention as defined by the following appended claims.

What is claimed is:

1. A method for determining cardiology disease risk from electrocardiogram trace data and clinical data, comprising:
   receiving electrocardiogram trace data associated with a patient;
   receiving clinical data associated with the patient;
   providing the electrocardiogram trace data and clinical data to a trained machine learning composite model comprising a plurality of clinical outcome prediction layers and a trained composite outcome prediction layer, each layer of the plurality of clinical outcome prediction layers being trained to evaluate the electrocardiogram trace data and the clinical data with respect to a corresponding cardiology disease and generate a cardiology disease risk score, the plurality of clinical outcome prediction layers including a layer for each disease of a set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness;
   providing the cardiology disease risk score for each of the plurality of clinical outcome prediction layers to the trained composite outcome prediction layer; and
   generating, by the trained composite outcome prediction layer and based at least in part on each cardiology disease risk score generated by the plurality of clinical outcome prediction layers, a composite risk score reflecting a likelihood of the patient being diagnosed with any cardiology disease of the set of cardiology diseases within a predetermined period of time from when the electrocardiogram trace data was generated; and
   outputting the composite risk score to at least one of a memory or a display.

2. The method of claim 1, wherein the clinical data comprises age and gender of the patient.

3. The method of claim 1, wherein the trained composite model is selected based at least in part on a severity of cardiology diseases the generated risk score represents.

4. The method of claim 3, wherein the severity of cardiology diseases include labels for one or more of normal, mild, moderate, and severe.

5. The method of claim 1, wherein the composite risk score is a classification based at least in part on a concatenation of the respective cardiology disease risk scores.

6. The method of claim 1, wherein the plurality of clinical outcome prediction layers are a plurality of convolutional neural networks.

7. The method of claim 1, wherein the predetermined period of time includes times at least one year from when the electrocardiogram trace data was generated.

8. The method of claim 1, wherein the trained composite model comprises training data associated with a plurality of clinical sites.

9. The method of claim 8, wherein the trained composite model comprises training the model using patient data associated with one site of the plurality of sites and testing the trained model on the remaining sites of the plurality of sites.

10. The method of claim 1, wherein the outputting the composite risk score further comprises outputting the composite risk score to a display of an electrocardiogram monitor.

11. The method of claim 1, wherein the outputting the composite risk score further comprises outputting the composite risk score to an electronic health records management system.

12. The method of claim 1, further comprising generating a supplementary risk score for one or more additional cardiology diseases, when the composite risk score exceeds a threshold.

13. The method of claim 12, wherein the composite risk score is associated with interventricular septal thickness.

14. The method of claim 13, wherein the one or more additional cardiology diseases comprises infiltrative diseases, hypertrophic cardiomyopathy, or concentric remodeling.

15. The method of claim 1, wherein the clinical data is selected from demographic data, vitals data, laboratory data, or comorbidities data.

16. The method of claim 15, wherein the vitals data comprises one or more of body mass index, systolic blood pressure, diastolic blood pressure, heart rate, height, weight, or smoking status.

17. The method of claim 15, wherein the laboratory data comprises one or more of A1C, bilirubin, blood urea nitrogen, cholesterol, creatine kinase myocardial band, creatinine, C-reactive protein, D-dimer, glucose, high-density lipoprotein, hemoglobin, high-density lipoprotein, lactate dehydrogenase, lymphocytes, potassium, pro B-type natriuretic peptide, sodium, troponin I and T, triglyceride, uric acid, very low-density lipoprotein, or estimated glomerular filtration rate.

18. The method of claim 15, wherein the comorbidities data comprises one or more of heart failure, prior myocardial infarction, diabetes mellitus, chronic obstructive pulmonary disease, renal failure, prior echocardiogram, coronary artery disease, or hypertension.

19. The method of claim 1, wherein the electrocardiogram trace data comprises ECG data selected from one or more of acute myocardial infarction, atrial fibrillation, atrial flutter, complete block, early repolarization, fascicular block, first-degree atrioventricular block, intraventricular conduction block, left bundle branch block, right bundle branch block, ischemia, left anterior descending artery ischemia, right bundle branch block, low QRS, left ventricular hypertrophy, non-specific ST-T wave, Non-specific T wave, other bradycardia, premature atrial contractions, pacemaker, poor tracing, prior infarction, prior myocardial infarction anterior, prolonged QT, premature ventricular contractions, right axis deviation, second degree atrioventricular block, sinus bradycardia, supraventricular tachycardia, tachycardia, tachyarrhythmia, T inversion, or ventricular tachycardia at a time when the electrocardiogram data was generated.

20. The method of claim 1, further comprising providing measurements from echocardiogram data to the trained composite model.

21. The method of claim 20, wherein the measurements from echocardiogram data comprises measurements selected from one or more of average R-R interval, P-R interval, P axis, QRS duration, QT, QTC, R axis, T axis, or ventricular rate.

22. The method of claim 1, further comprising gathering the clinical data and electrocardiogram trace data based at least in part on a presence of ICD codes associated with the patient.

23. The method of claim 1, wherein the electrocardiogram trace data comprises at least 8 leads.

24. The method of claim 1, wherein the electrocardiogram trace data is sampled at 250 hz or 500 hz.

25. The method of claim 1, wherein training the trained composite model comprises:
receiving training data associated with a plurality of patients, each of the patients having received an echocardiogram;
generating a patient timeline for each patient of the plurality of patients;
anchoring each respective patient timeline to a date of occurrence of an echocardiogram; and
labeling each respective patient as having a positive or negative ECG based at least in part on the date of an ECG with respect to the date of occurrence of the echocardiogram.

26. The method of claim 25, further comprising:
excluding patients from training after a censoring event is detected in the patient timeline.

27. The method of claim 1, further comprising, when the composite risk score exceeds a predetermined threshold:
generating a notification to provide additional monitoring of the patient, the additional monitoring including an echocardiogram.

28. A system comprising:
a computer including a processing device, the processing device configured to:
receive electrocardiogram trace data associated with a patient;
receive clinical data of the patient;
provide the electrocardiogram trace data and clinical data to a trained composite model comprising a plurality of clinical outcome prediction layers and a trained composite outcome prediction layer, each layer of the plurality of clinical outcome prediction layers being trained to generate a cardiology disease risk score for a respective cardiology disease based on the electrocardiogram trace data and the clinical data; wherein the plurality of clinical outcome prediction layers includes a layer for each of a set of cardiology diseases, the set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness;
provide the cardiology disease risk score for each of the plurality of clinical outcome prediction layers to the trained composite outcome prediction layer; and
receive a composite risk score indicative of a likelihood the patient will suffer from any of the diseases in the set of cardiology diseases within a predetermined period of time from when the electrocardiogram trace data was generated, the composite risk score being generated at the trained composite outcome prediction layer based at least in part on each cardiology risk score for each of the plurality of clinical outcome prediction layers; and output the composite risk score to at least one of a memory or a display.

29. A non-transitory computer readable medium, comprising instructions for causing a computer to:

receive electrocardiogram trace data associated with a patient;

receive clinical data of the patient;

provide the electrocardiogram trace data and clinical data to a trained composite model comprising a plurality of clinical outcome prediction layers and a trained composite outcome prediction layer, each layer of the plurality of clinical outcome prediction layers being trained to generate a corresponding cardiology disease risk score based on the electrocardiogram trace data and the clinical data with respect to a corresponding cardiology disease; wherein plurality of clinical outcome prediction layers including a layer for each of a set of cardiology diseases, the set of cardiology diseases comprising three or more of cardiac amyloidosis, aortic stenosis, aortic regurgitation, mitral stenosis, mitral regurgitation, tricuspid regurgitation, abnormal reduced ejection fraction (EF), or abnormal interventricular septal thickness;

provide the cardiology disease risk score for each of the plurality of clinical outcome prediction layers to the trained composite outcome prediction layer; and receive a composite risk score, the composite risk score being generated at the trained composite outcome prediction layer based in part on each cardiology disease risk score and the composite risk score being indicative of a likelihood the patient will suffer from any of the diseases in the set of cardiology diseases within a predetermined period of time from when the electrocardiogram trace data was generated; and output the composite risk score to at least one of a memory or a display.

* * * * *